(12) United States Patent
Benson et al.

(10) Patent No.: US 8,153,663 B2
(45) Date of Patent: Apr. 10, 2012

(54) 3-AMINO-INDAZOLE OR 3-AMINO-4,5,6,7-TETRAHYDRO-INDAZOLE DERIVATIVES

(75) Inventors: Gregory Martin Benson, Therwil (CH); Konrad Bleicher, Freiburg (DE); Song Feng, Shanghai (CN); Uwe Grether, Efringen-Kirchen (DE); Bernd Kuhn, Reinach (CH); Rainer E. Martin, Basel (CH); Jean-Marc Plancher, Hagenthal-le-Bas (FR); Hans Richter, Grenzach-Wyhlen (DE); Markus Rudolph, Basel (CH); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 127 days.

(21) Appl. No.: 12/563,189

(22) Filed: Sep. 21, 2009

(65) Prior Publication Data
US 2010/0076026 A1 Mar. 25, 2010

(30) Foreign Application Priority Data
Sep. 25, 2008 (EP) ..................... 08165137

(51) Int. Cl.
- A61K 31/44 (2006.01)
- A61K 31/415 (2006.01)
- C07D 401/02 (2006.01)
- C07D 231/56 (2006.01)

(52) U.S. Cl. ............... 514/338; 514/407; 546/275.7; 548/360.1

(58) Field of Classification Search .......... 514/338, 514/407; 546/275.7; 548/360.1
See application file for complete search history.

(56) References Cited

FOREIGN PATENT DOCUMENTS

| | | |
|---|---|---|
| EP | 1698335 | 9/2006 |
| GB | 926 327 | 5/1963 |
| GB | 1145544 | 3/1969 |
| WO | WO 01/98282 | 12/2001 |
| WO | WO 2004/041822 | 5/2004 |
| WO | WO 2004/050651 | 6/2004 |
| WO | WO 2007/569091 | 5/2007 |
| WO | WO 2007/064872 | 6/2007 |

OTHER PUBLICATIONS

Alkhader, Mohamed. Synthesis of Some Newer Indazolyl-Oxadiazoles, Thiadiazoles, and 1,2,4-Triazoles. Qatar Univ. Sci. J. 14 (1994): 114-122.*
Ahn et al., Org. Biomol. Chem., 5, pp. 2472-2485 (2007).
Shirtcliff et al., J. Org. Chem., 71, pp. 6619-6622 (2006).
Ardakani et al., Synthesis, 4, pp. 308-309 (1979).
Chung et al., Bioorganic & Medicinal Chem., 15, pp. 6043-6053 (2007).
Barral et al., Organic Letters, 9, pp. 1809-1811 (2007).
Han, R et al, *Tetrahedron Letters*, 47:41 7295-77299, (2006) XP005636896.
Quast, H et al, *Chemische Berichte*, 118:6 (1985) XP007910837, (1985).
Stadlbauer, W. *Science of Synthesis*, 12:227-324 (2002) XP001179192.

* cited by examiner

*Primary Examiner* — Rebecca Anderson
*Assistant Examiner* — Samantha Shterengarts
(74) *Attorney, Agent, or Firm* — George W. Johnston; Patricia S. Rocha-Tramaloni

(57) ABSTRACT

This invention relates to novel indazole derivatives of formula I:

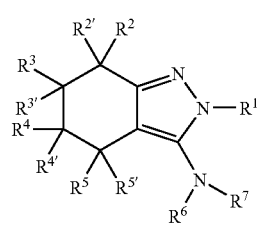

wherein $R^1$ to $R^7$ are as defined in the description and in the claims, as well as physiologically acceptable salts thereof. These compounds are FXR modulators and can be used as medicaments.

20 Claims, No Drawings

3-AMINO-INDAZOLE OR 3-AMINO-4,5,6,7-TETRAHYDRO-INDAZOLE DERIVATIVES

PRIORITY TO RELATED APPLICATION(S)

This application claims the benefit of European Patent Application No. 08165137.4, filed Sep. 25, 2008, which is hereby incorporated by reference in its entirety.

BACKGROUND OF THE INVENTION

The farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. (1999). Identification of a nuclear receptor for bile acids. Science 284, 1362-5]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXR alpha and blocks their transcriptional functions [Lu, T. T., Makishima, M., Repa, J. J., Schoonjans, K., Kerr, T. A., Auwerx, J. and Mangelsdorf, D. J. (2000). Molecular basis for feedback regulation of bile acid synthesis by nuclear receptors. Mol Cell 6, 507-15]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Taff, P. T., Jones, S. A., Anisfeld, A. M., Stoltz, C. M., Tontonoz, P., Kliewer, S., Willson, T. M. and Edwards, P. A. (2002). Regulation of multidrug resistance-associated protein 2 (ABCC2) by the nuclear receptors pregnane X receptor, farnesoid X-activated receptor, and constitutive androstane receptor. J Biol Chem 277, 2908-15; Ananthanarayanan, M., Balasubramanian, N., Makishima, M., Mangelsdorf, D. J. and Suchy, F. J. (2001). Human bile salt export pump promoter is transactivated by the farnesoid X receptor/bile acid receptor. J Biol Chem 276, 28857-65]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. (2003). Hepatoprotection by the farnesoid X receptor agonist GW4064 in rat models of intra- and extrahepatic cholestasis. J Clin Invest 112, 1678-87; Sinal, C. J., Tohkin, M., Miyata, M., Ward, J. M., Lambert, G. and Gonzalez, F. J. (2000). Targeted disruption of the nuclear receptor FXR/BAR impairs bile acid and lipid homeostasis. Cell 102, 731-44]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines the hydrophilicity of the bile acid pool and its ability to solubilize cholesterol. FXR activation increases the hydrophilicity of the pool, decreasing the intestinal solubilization of cholesterol, effectively blocking its absorption. Decrease absorption would be expected to result in lowering of plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. (2006) Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. J Biol Chem 281, 807-12]. FXR also decreases hepatic synthesis of triglycerides by repressing SREBP1-c expression by an alternate pathway involving SHP and LXRalpha. Thus compounds which modulate FXR activity may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol >240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple co-morbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

SUMMARY OF THE INVENTION

The present invention is concerned with 3-amino-indazole or 3-amino-4,5,6,7-tetrahydro-indazole derivatives, their manufacture, pharmaceutical compositions containing them and their use as medicaments. In particular, the present invention relates to compounds of the formula

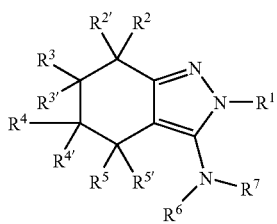

I and pharmaceutically acceptable salts thereof, wherein $R^1$-$R^7$ and $R^{2'}$-$R^{5'}$ are as defined in the detailed description and claims. The compounds of the present invention are selective modulators of the farnesoid-X-receptor, preferably agonists of the farnesoid-X-receptor. The novel compounds of the present invention exceed the compounds known in the art, inasmuch as they bind to and selectively modulate FXR very efficiently. Consequently, cholesterol absorption is reduced, LDL cholesterol and triglycerides are lowered, and inflammatory atherosclerosis is reduced. Since multiple facets of combined dyslipidemia and cholesterol homeostasis are addressed by FXR modulators, they are expected to have an enhanced therapeutic potential compared to the compounds already known in the art.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "hydrogen" or "hydro" refers to the moiety of a hydrogen atom (—H) and not $H_2$.

The term "halogen" refers to fluoro, chloro, bromo or iodo. Preferred "halogen" groups are fluoro, chloro and bromo.

The term "alkyl", alone or in combination with other groups, refers to a branched or straight-chain monovalent saturated aliphatic hydrocarbon radical of one to twenty carbon atoms. In preferred embodiments, the alkyl has one to sixteen carbon atoms, and more preferably one to ten carbon atoms. The term "$C_{1-10}$-alkyl" refers to a branched or straight-chain monovalent saturated aliphatic hydrocarbon radical of one to ten carbon atoms, such as methyl, ethyl, n-propyl, isopropyl, n-butyl, s-butyl, t-butyl, pentyl, 1,1,3,3-tetramethyl-butyl and the like. Lower alkyl groups as described below also are preferred alkyl groups.

The term "lower alkyl" or "$C_{1-7}$-alkyl", alone or in combination with other groups, signifies a straight-chain or branched-chain alkyl group with 1 to 7 carbon atoms. In preferred embodiments the lower alkyl is a straight or branched-chain alkyl group with 1 to 6 carbon atoms and particularly preferred a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls. In certain preferred embodiments the lower alkyl is methyl or ethyl with methyl being the most preferred.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by cycloalkyl. An example is cyclopropyl-methyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec-butoxy and tert-butoxy. In particular embodiments the lower alkoxy is methoxy or ethoxy.

The term "cycloalkyloxy" or "$C_{3-7}$-cycloalkyloxy" refers to the group R"—O—, wherein R" is cycloalkyl. Examples of cycloalkyloxy groups are cyclopropyloxy, cyclobutyloxy, cyclopentyloxy, cyclohexyloxy and cycloheptyloxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by an alkoxy group, wherein said alkoxy group may further be substituted by an additional alkoxy group. Among the preferred lower alkoxyalkyl groups are 1-methoxymethyl, 2-methoxyethyl, 3-methoxypropyl and 2-(2-methoxyethoxy)-ethyl.

The term "lower halogenalkyl" or "halogen-$C_{1-7}$-alkyl" refers to lower alkyl groups as defined above wherein at least one of the hydrogen atoms of the lower alkyl group is replaced by a halogen atom. In some preferred embodiments the halogen is fluoro or chloro, and most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom. In some preferred embodiments the halogen is fluoro or chloro, and most preferably fluoro. Among the preferred halogenated lower alkoxy groups are trifluoromethoxy, difluoromethoxy, fluormethoxy and chloromethoxy, with trifluoromethoxy being especially preferred.

The term "carboxyl" means the group —COOH.

The term "lower alkoxycarbonyl" or "$C_{1-7}$-alkoxycarbonyl" refers to the group —CO—OR' wherein R' is lower alkyl and the term "lower alkyl" has the previously given significance. Preferred lower alkoxycarbonyl groups are methoxycarbonyl or ethoxycarbonyl.

The term "lower alkoxycarbonylalkyl" or "$C_{1-7}$-alkoxycarbonyl-$C_{1-7}$-alkyl" means a lower alkyl group as defined above wherein one of the hydrogen atoms of the lower alkyl group is replaced by a $C_{1-7}$-alkoxycarbonyl. A preferred lower alkoxycarbonylalkyl group is —$CH_2$—$COOCH_3$.

The term "lower alkoxycarbonylalkoxy" or "$C_{1-7}$-alkoxycarbonyl-$Cl_{1-7}$-alkoxy" refers to a lower alkoxy group as defined above wherein one of the hydrogen atoms of the lower alkoxy group is replaced by a $C_{1-7}$-alkoxycarbonyl. A preferred lower alkoxycarbonylalkoxy group is t-butoxycarbonylmethoxy (—O—CH$_2$—COO—C(CH$_3$)$_3$).

The term "lower carboxylalkyl" or "carboxyl-C$_{1-7}$-alkyl" refers to a lower alkyl group as defined above wherein at least one of the hydrogen atoms of the lower alkyl group is replaced by a carboxyl group. Among the preferred lower carboxyl alkyl groups are carboxylmethyl (—CH$_2$—COOH) and carboxylethyl (—CH$_2$—CH$_2$—COOH), with carboxylmethyl being especially preferred.

The term "lower carboxylalkoxy" or "carboxyl-C$_{1-7}$-alkoxy" refers to a lower alkoxy group as defined above wherein at least one of the hydrogen atoms of the lower alkoxy group is replaced by a carboxyl group. A preferred lower carboxylalkoxy group is carboxylmethoxy (—O—CH$_2$—COOH).

The term "heteroaryl" refers to an aromatic 5 to 6 membered monocyclic ring or 9 to 10 membered bicyclic ring which can comprise 1, 2 or 3 atoms selected from nitrogen, oxygen and sulphur. Examples include furyl, pyridyl, 2-oxo-1,2-dihydro-pyridyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzoimidazolyl, indolyl, isoindolyl, 1,3-dioxo-isoindolyl, quinolinyl, indazolyl, benzoisothiazolyl, benzoxazolyl, benzoisoxazolyl, benzothiophenyl, benzothiazolyl, benzofuranyl and quinoxalinyl. Preferred heteroaryl groups are pyridyl, pyrimidinyl, oxazolyl, benzodioxolyl, thiophenyl, pyrrolyl, 2-oxo-1,2-dihydro-pyridinyl, indolyl, quinolinyl, 1,3-dioxo-isoindolyl, imidazolyl, benzothiophenyl, benzothiazolyl, benzofuranyl, quinoxalinyl, pyrazolyl, isoxazolyl, benzimidazolyl and furyl, with pyridyl being most preferred.

The term "heterocyclyl" refers to a 5 to 6 membered monocyclic ring or 8 to 10 membered bi- or tricyclic ring which can comprise 1, 2 or 3 atoms selected from nitrogen, oxygen and sulphur. Examples include morpholinyl, thiomorpholinyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl, piperazinyl, tetrahydrofuranyl and tetrahydropyranyl. Preferred heterocyclyl groups are tetrahydrofuranyl and tetrahydropyranyl.

The term "protecting group" refers to groups which are used to protect functional groups, particularly hydroxy groups, temporarily. Examples of protecting groups are benzyl, p-methoxybenzyl, t-butyl-dimethylsilyl, t-butyl-diphenylsilyl and (for protection of amino groups) Boc and benzyloxycarbonyl.

Compounds of formula I can form pharmaceutically acceptable salts. Examples of such pharmaceutically acceptable salts are acid addition salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I in which a COOH group is present can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, in reference to a particular group or molecule, the term "substituted" refers to the fact that at least one of the hydrogen atoms of that group or molecule is replaced by some other substituent.

Unless otherwise indicated, the term "a compound of the formula" or "a compound of formula" or "compounds of the formula" or "compounds of formula" refers to any compound selected from the genus of compounds as defined by the formula.

In detail, the present invention relates to compounds of the formula:

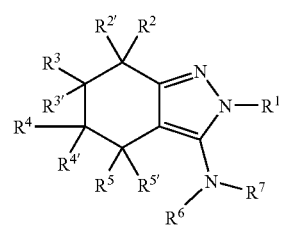

or a pharmaceutically acceptable salt thereof, wherein:

$R^1$ is a ring selected from the group consisting of phenyl, naphthyl and heteroaryl, said ring being unsubstituted or substituted with 1 to 3 substituents independently selected from the group consisting of: (1) lower alkyl, (2) halogen, (3) lower halogenalkyl, (4) hydroxy, (5) lower alkoxy, (6) lower halogenalkoxy and (7) cyano;

$R^2$, $R^3$, $R^4$ and $R^5$ independently from each other are selected from the group consisting of hydrogen, halogen and lower alkyl;

$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;

$R^6$ is selected from the group consisting of:
  (1) lower alkyl,
  (2) cycloalkyl,
  (3) lower alkoxyalkyl,
  (4) unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, lower alkoxycarbonyl, lower alkoxycarbonylalkyl, lower carboxylalkoxy, lower alkoxycarbonylalkoxy and cyano,
  (5) lower phenylalkyl, wherein the phenyl group is unsubstituted or substituted with 1 to 3 substituents independently selected from the group consisting of lower alkyl, halogen, lower halogenalkyl, hydroxy, lower alkoxy, lower halogenalkoxy and cyano,
  (6) heterocyclyl, and
  (7) unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano;

$R^7$ is selected from the group consisting of (1) hydrogen, (2) —C(O)—NH—$R^8$, (3) —C(O)—$R^9$, (4) —S(O)$_2$—$R^{10}$, and (5) —C(O)—O$R^{11}$;

$R^8$ is selected from the group consisting of:
(1) lower alkyl,
(2) cycloalkyl,
(3) lower cycloalkylalkyl,
(4) cycloalkyl substituted by hydroxy, carboxyl, tetrazolyl or lower carboxylalkyl,
(5) heterocyclyl, and
(6) unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;

$R^9$ is selected from the group consisting of:
(1) lower alkyl,
(2) cycloalkyl,
(3) lower cycloalkylalkyl, and
(4) lower phenylalkyl, wherein the phenyl group of said lower phenylalkyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;

$R^{10}$ is selected from the group consisting of:
(1) lower alkyl,
(2) cycloalkyl,
(3) lower cycloalkylalkyl, and
(4) lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl; and $R^{11}$ is selected from the group consisting of:
(1) lower alkyl,
(2) cycloalkyl,
(3) lower cycloalkylalkyl,
(4) cycloalkyl substituted by hydroxy, carboxyl, tetrazolyl or lower carboxylalkyl,
(5) heterocyclyl, and
(6) unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl.

Compounds of formula I are individually preferred and physiologically acceptable salts thereof are individually preferred, with the compounds of formula I being particularly preferred.

Preferred are further compounds of formula I according to the present invention, wherein $R^1$ is a phenyl ring, said ring being unsubstituted or substituted with 1 to 3 substituents independently selected from the group consisting of lower alkyl, halogen, lower halogenalkyl, hydroxy, lower alkoxy, lower halogenalkoxy and cyano. Especially preferred are the compounds of formula I according to the invention, wherein $R^1$ is phenyl or phenyl substituted with halogen.

Further preferred compounds of formula I according to the invention are those, wherein $R^2$, $R^3$, $R^4$ and $R^5$ independently from each other are selected from hydrogen or halogen. Especially preferred are compounds of formula I, wherein $R^2$, $R^3$, $R^4$ and $R^5$ are hydrogen. In addition, compounds of formula I are especially preferred, wherein $R^3$ is halogen, preferably fluoro, and $R^2$, $R^4$ and $R^5$ are hydrogen or wherein $R^4$ is halogen, preferably chloro, and $R^2$, $R^3$ and $R^5$ are hydrogen. Furthermore, compounds of formula I are especially preferred, wherein $R^3$ and $R^4$ are halogen, preferably fluoro, and $R^2$ and $R^5$ are hydrogen.

Preferred are further compounds of formula I of the present invention, wherein $R^{2'}$ and $R^{3'}$ together as well as $R^{4'}$ and $R^{5'}$ together are replaced by a double bond, meaning these are compounds having the formula

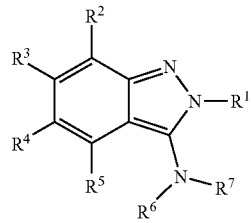

Ia wherein $R^1$ to $R^7$ are as defined herein before.

Another group of preferred compounds of formula I of the present invention are those, $R^{2'}$, $R^{3'}$, $R^{4'}$ and $R^{5'}$ are hydrogen, with those compounds being especially preferred, wherein also $R^2$, $R^3$, $R^4$ and $R^5$ are hydrogen, meaning compounds having the formula

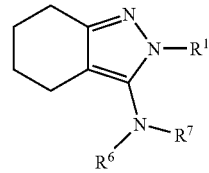

Ib wherein $R^1$, $R^6$ and $R^7$ are as defined herein before.

Furthermore, compounds of formula I according to the invention are preferred, wherein $R^6$ is selected from the group consisting of lower alkyl, cycloalkyl, lower alkoxyalkyl, unsubstituted phenyl or phenyl substituted with 1 to 3 substituents independently selected from the group consisting of lower alkyl, halogen, lower halogenalkyl, lower alkoxy, lower halogenalkoxy and cyano, lower phenylalkyl, heterocyclyl selected from tetrahydrofuranyl and tetrahydropyranyl, and pyridyl.

Especially preferred are compounds of formula I, wherein $R^6$ is cycloalkyl, with those compounds of formula I being more preferred, wherein $R^6$ is $C_4$-$C_6$-cycloalkyl, and those compounds of formula I being most preferred, wherein $R^6$ is cyclohexyl. Especially preferred are furthermore compounds of formula I, wherein $R^6$ is lower alkyl, with those compounds being more preferred, wherein $R^6$ is $C_3$-$C_7$-alkyl, and those compounds being most preferred wherein $R^6$ is $C_4$-$C_6$-alkyl.

Also especially preferred are compounds of formula I, wherein $R^6$ is unsubstituted phenyl or phenyl substituted with 1 to 3 substituents independently selected from the group consisting of lower alkyl, halogen, lower halogenalkyl, lower alkoxy, lower halogenalkoxy and cyano, with those compounds being more preferred, wherein $R^6$ is unsubstituted phenyl or phenyl substituted with 1 or 2 substituents independently selected from halogen and lower alkoxy.

Further preferred compounds of formula I of the present invention include compounds, wherein $R^6$ is selected from lower phenylalkyl, preferably benzyl, or heteroaryl, preferably pyridyl. Furthermore, compounds of formula I are preferred, wherein $R^6$ is heterocyclyl, preferably tetrahydrofuranyl or tetrahydropyranyl.

In addition, compounds of formula I according to the invention are preferred, wherein $R^7$ is hydrogen.

Also preferred are compounds of formula I according to any one of claims 1 to 8, wherein $R^7$ is —C(O)—NH—$R^8$ and $R^8$ is selected from the group consisting of lower alkyl, cycloalkyl, lower cycloalkylalkyl, cycloalkyl substituted by hydroxy, carboxyl, tetrazolyl or lower carboxylalkyl, heterocyclyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl. Within this group, compounds of formula I are more preferred, wherein $R^8$ is cycloalkyl, cycloalkyl substituted by hydroxy, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, lower alkoxycarbonyl, lower alkoxycarbonylalkyl, lower carboxylalkyl, lower carboxylalkoxy and lower alkoxycarbonylalkoxy, with those compounds of formula I being most preferred, wherein $R^8$ is cycloalkyl or cycloalkyl substituted by hydroxy. Also preferred are those compounds, wherein $R^8$ is unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, lower alkoxycarbonyl, lower alkoxycarbonylalkyl, lower carboxylalkyl, lower carboxylalkoxy and lower alkoxycarbonylalkoxy.

Another group of preferred compounds of formula I according to the present invention are those, wherein $R^7$ is —C(O)—$R^9$ and $R^9$ is selected from the group consisting of lower alkyl, cycloalkyl, lower cycloalkylalkyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl. More preferably, $R^9$ is lower cycloalkylalkyl.

Further preferred are compounds of formula I according to the invention, wherein $R^7$ is —S(O)$_2$—$R^{10}$ and $R^{10}$ is selected from the group consisting of lower alkyl, cycloalkyl, lower cycloalkylalkyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl. More preferably, $R^{10}$ is lower cycloalkylalkyl.

Preferred are also compounds of formula I according to the invention, wherein $R^7$ is —C(O)—O$R^{11}$ and $R^{11}$ is selected from the group consisting of lower alkyl, cycloalkyl, lower cycloalkylalkyl, cycloalkyl substituted by hydroxy, carboxyl, tetrazolyl or lower carboxylalkyl, heterocyclyl, unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group is substituted by carboxyl. More preferably, $R^{11}$ is cycloalkyl or cycloalkyl substituted by hydroxy.

Particularly preferred compounds of formula I of the invention are selected from the group consisting of:
1,3-dicyclohexyl-1-(2-phenyl-2H-indazol-3-yl)-urea,
4-[3-cyclohexyl-3-(2-phenyl-2H-indazol-3-yl)-ureido]-benzoic acid,
1-cyclohexyl-3-(2-fluoro-phenyl)-1-(2-phenyl-2H-indazol-3-yl)-urea,
1-butyl-1-[2-(4-chloro-phenyl)-2H-indazol-3-yl]-3-cyclohexyl-urea,
1-cyclohexyl-3-(2,6-dimethyl-phenyl)-1-(2-phenyl-2H-indazol-3-yl)-urea,
benzyl-(2-phenyl-2H-indazol-3-yl)-amine,
1-benzyl-1-[2-(4-chloro-phenyl)-2H-indazol-3-yl]-3-cyclohexyl-urea,
3-[3-cyclohexyl-3-(2-phenyl-2H-indazol-3-yl)-ureido]-benzoic acid,
4-{3-benzyl-3-[2-(4-chloro-phenyl)-2H-indazol-3-yl]-ureido}-3-chloro-benzoic acid,
1-[2-(4-chloro-phenyl)-2H-indazol-3-yl]-3-cyclohexyl-1-(tetrahydro-pyran-4-yl)-urea,
1-[2-(4-chloro-phenyl)-2H-indazol-3-yl]-1,3-dicyclohexyl-urea,
4-{3-butyl-3-[2-(4-chloro-phenyl)-2H-indazol-3-yl]-ureido}-3-chloro-benzoic acid,
4-[3-cyclohexyl-3-(2-phenyl-2H-indazol-3-yl)-ureido]-3-methyl-benzoic acid,
3-chloro-4-[3-cyclohexyl-3-(2-phenyl-2H-indazol-3-yl)-ureido]-benzoic acid,
1-[2-(4-chloro-phenyl)-2H-indazol-3-yl]-3-cyclohexyl-1-phenyl-urea,
3-chloro-4-{3-[2-(4-chloro-phenyl)-5,6-difluoro-2H-indazol-3-yl]-3-cyclohexyl-ureido}-benzoic acid,
1-[2-(4-chloro-phenyl)-2H-indazol-3-yl]-3-cyclohexyl-1-(2-methoxy-ethyl)-urea,
3-chloro-4-{3-[2-(4-chloro-phenyl)-2H-indazol-3-yl]-3-phenyl-ureido}-benzoic acid methyl ester,
1-(3-chloro-phenyl)-1-[2-(4-chloro-phenyl)-2H-indazol-3-yl]-3-cyclohexyl-urea,
3-chloro-4-[3-[2-(4-chloro-phenyl)-2H-indazol-3-yl]-3-(2-methoxy-ethyl-ureido]-benzoic acid,
(3-chloro-4-{3-[2-(4-chloro-phenyl)-2H-indazol-3-yl]-3-cyclohexyl-ureido}-phenyl)-acetic acid,
4-{3-[2-(4-chloro-phenyl)-2H-indazol-3-yl]-3-cyclohexyl-ureido}-3-methyl-benzoic acid,
3-chloro-4-{3-[2-(4-chloro-phenyl)-2H-indazol-3-yl]-3-cyclohexyl-ureido}-benzoic acid,
{4-[3-cyclohexyl-3-(2-phenyl-2H-indazol-3-yl)-ureido]-3-fluoro-phenoxy}-acetic acid, 1-[2-(4-chloro-phenyl)-2H-indazol-3-yl]-3-cyclohexyl-1-(3-ethoxy-phenyl)-urea,
3-(4-{3-[2-(4-chloro-phenyl)-2H-indazol-3-yl]-3-cyclohexyl-ureido}-3-fluoro-phenyl)-propionic acid,
3-{3-[2-(4-chloro-phenyl)-2H-indazol-3-yl]-3-cyclohexyl-ureido}-2-methyl-benzoic acid,
1-(3-chloro-4-fluoro-phenyl)-1-[2-(4-chloro-phenyl)-2H-indazol-3-yl]-3-cyclohexyl-urea,
1-[5-chloro-2-(4-chloro-phenyl)-2H-indazol-3-yl]-3-cyclohexyl-1-(3-ethoxy-phenyl)-urea,
(4-{3-[2-(4-chloro-phenyl)-2H-indazol-3-yl]-3-cyclohexyl-ureido}-3-fluoro-phenoxy)-acetic acid methyl ester,
3-chloro-4-{3-[2-(4-chloro-phenyl)-2H-indazol-3-yl]-3-cyclobutyl-ureido}-benzoic acid,
2-(4-{3-[2-(4-chloro-phenyl)-2H-indazol-3-yl]-3-cyclohexyl-ureido}-3-fluoro-phenyl)-2-methyl-propionic acid,
3-{3-[2-(4-chloro-phenyl)-2H-indazol-3-yl]-3-cyclohexyl-ureido}-4-methyl-benzoic acid,
N-[2-(4-chloro-phenyl)-2H-indazol-3-yl]-C-dicyclohexyl-methanesulfonamide,
1-(3-chloro-phenyl)-1-[2-(3-chloro-phenyl)-6-fluoro-2H-indazol-3-yl]-3-cyclohexyl-urea,
N-[2-(4-chloro-phenyl)-2H-indazol-3-yl]-2,N-dicyclohexyl-acetamide,
[2-(4-chloro-phenyl)-2H-indazol-3-yl]-cyclohexyl-carbamic acid cyclohexyl ester,
1-[2-(4-chloro-phenyl)-2H-indazol-3-yl]-1,3-dicyclopentyl-urea,
N-[2-(4-chloro-phenyl)-2H-indazol-3-yl]-N-cyclohexyl-2-phenyl-acetamide,
1-[2-(4-chloro-phenyl)-6-fluoro-2H-indazol-3-yl]-1,3-dicyclohexyl-urea,
trans-1-(3-chloro-phenyl)-1-[2-(4-chloro-phenyl)-2H-indazol-3-yl]-3-(4-hydroxy-cyclohexyl)-urea,
1-[2-(4-chloro-phenyl)-2H-indazol-3-yl]-3-cyclohexyl-1-pyridin-3-yl-urea,
1-(3-chloro-phenyl)-1-[2-(3-chloro-phenyl)-5,6-difluoro-2H-indazol-3-yl]-3-cyclohexyl-urea,
1-(3-chloro-phenyl)-1-[2-(4-chloro-phenyl)-6-fluoro-2-yl]-3-cyclohexyl-urea, cyclohexyl-(2-phenyl-4,5,6,7-tetrahydro-2H-indazol-3-yl)-amine,
1,3-dicyclohexyl-1-(2-phenyl-4,5,6,7-tetrahydro-2H-indazol-3-yl)-urea,
3-chloro-4-[3-cyclohexyl-3-(2-phenyl-4,5,6,7-tetrahydro-2H-indazol-3-yl)-ureido]-benzoic acid,
and pharmaceutically acceptable salts thereof.

Especially preferred compounds of formula I are those selected from the group consisting of:
1-cyclohexyl-3-(2-fluoro-phenyl)-1-(2-phenyl-2H-indazol-3-yl)-urea,
1-butyl-1-[2-(4-chloro-phenyl)-2H-indazol-3-yl]-3-cyclohexyl-urea,
4-{3-benzyl-3-[2-(4-chloro-phenyl)-2H-indazol-3-yl]-ureido}-3-chloro-b enzoic acid,
1-[2-(4-chloro-phenyl)-2H-indazol-3-yl]-3-cyclohexyl-1-(tetrahydro-pyran-4-yl)-urea,
1-[2-(4-chloro-phenyl)-2H-indazol-3-yl]-1,3-dicyclohexyl-urea,
1-[2-(4-chloro-phenyl)-2H-indazol-3-yl]-3-cyclohexyl-1-phenyl-urea,
3-chloro-4-{3-[2-(4-chloro-phenyl)-5,6-difluoro-2H-indazol-3-yl]-3-cyclohexyl-ureido}-benzoic acid,
1-(3-chloro-phenyl)-1-[2-(4-chloro-phenyl)-2H-indazol-3-yl]-3-cyclohexyl-urea,
(3-chloro-4-{3-[2-(4-chloro-phenyl)-2H-indazol-3-yl]-3-cyclohexyl-ureido}-phenyl)-acetic acid,
3-(4-{3-[2-(4-chloro-phenyl)-2H-indazol-3-yl]-3-cyclohexyl-ureido}-3-fluoro-phenyl)-propionic acid,
1-(3-chloro-4-fluoro-phenyl)-1-[2-(4-chloro-phenyl)-2H-indazol-3-yl]-3-cyclohexyl-urea,
1-(3-chloro-phenyl)-1-[2-(3-chloro-phenyl)-6-fluoro-2H-indazol-3-yl]-3-cyclohexyl-urea,
N-[2-(4-chloro-phenyl)-2H-indazol-3-yl]-2,N-dicyclohexyl-acetamide,
[2-(4-chloro-phenyl)-2H-indazol-3-yl]-cyclohexyl-carbamic acid cyclohexyl ester,
1-[2-(4-chloro-phenyl)-6-fluoro-2H-indazol-3-yl]-1,3-dicyclohexyl-urea,
trans-1-(3-chloro-phenyl)-1-[2-(4-chloro-phenyl)-2H-indazol-3-yl]-3-(4-hydroxy-cyclohexyl)-urea,
1,3-dicyclohexyl-1-(2-phenyl-4,5,6,7-tetrahydro-2H-indazol-3-yl)-urea,
3-chloro-4-[3-cyclohexyl-3-(2-phenyl-4,5,6,7-tetrahydro-2H-indazol-3-yl)-ureido]-benzoic acid,
and pharmaceutically acceptable salts thereof.

Even more preferred compounds of formula I are those selected from the group consisting of:
1-[2-(4-chloro-phenyl)-2H-indazol-3-yl]-1,3-dicyclohexyl-urea,
3-chloro-4-{3-[2-(4-chloro-phenyl)-5,6-difluoro-2H-indazol-3-yl]-3-cyclohexyl-ureido}-benzoic acid,
1-(3-chloro-phenyl)-1-[2-(3-chloro-phenyl)-6-fluoro-2H-indazol-3-yl]-3-cyclohexyl-urea,
1-[2-(4-chloro-phenyl)-6-fluoro-2H-indazol-3-yl]-1,3-dicyclohexyl-urea,
trans-1-(3-chloro-phenyl)-1-[2-(4-chloro-phenyl)-2H-indazol-3-yl]-3-(4-hydroxy-cyclohexyl)-urea,
1,3-dicyclohexyl-1-(2-phenyl-4,5,6,7-tetrahydro-2H-indazol-3-yl)-urea,
and pharmaceutically acceptable salts thereof.

The invention also relates to a process for the manufacture of compounds of formula I as defined above, which process comprises a) reductive amination of a compound of the formula II

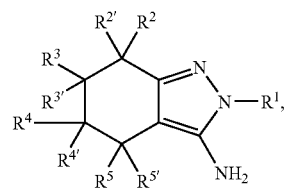

wherein $R^1$ to $R^{5'}$ are as defined herein before, with a ketone or aldehyde of the formula III $$O=CR^xR^y \qquad\qquad III,$$

wherein $CR^xR^y$ corresponds to $R^6$ selected from the group consisting of lower alkyl, cycloalkyl, lower alkoxyalkyl, heterocyclyl, and lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano, in the presence of a reducing agent and an acid to obtain a compound of formula Ic

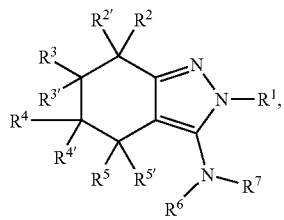

wherein $R^1$ to $R^6$ are as defined above and $R^7$ is hydrogen, and, if desired, b) transferring the compound of formula Ic into a compound of formula I, wherein $R^7$ is selected from a group consisting of —C(O)—NH—$R^8$, —C(O)—$R^9$, —S(O)$_2$—$R^{10}$ and —C(O)—O$R^{11}$ as defined herein before, and, if desired, c) converting the compound obtained into a pharmaceutically acceptable salt.

Appropriate reducing agents are for example sodium borohydride, sodium cyanoborohydride and sodium triacetoxyborohydride, with sodium triacetoxyborohydride being preferred. Appropriate acids are for example acetic acid, boric acid or p-toluenesulfonic acid monohydrate, with acetic acid being preferred. The reaction is carried out in a suitable solvent such as for example dichloromethane at temperature in the range of −20° C. to reflux temperature of the solvent.

"Transferring the compound of formula Ic into a compound of formula I, wherein $R^7$ is selected from a group consisting of —C(O)—NH—$R^8$, —C(O)—$R^9$, —S(O)$_2$—$R^{10}$ and —C(O)—O$R^{11}$" means employing one of the reactions as described in Scheme A below under steps c, d, e or f, i.e. reacting the compound of formula Ic with an isocyanide of formula VI or an acid chloride of formula VII or a sulfonyl chloride of formula VIII or a chloroformate of formula IX under appropriate conditions.

The invention further relates to a process for the manufacture of compounds of formula I as defined above, which process comprises a) nucleophilic aromatic substitution of a compound of the formula IV

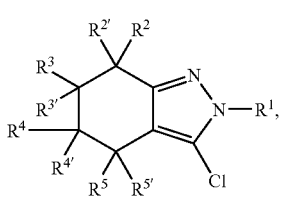

wherein $R^1$ to $R^{5'}$ are as defined herein before, with an amine of the formula V $$R^6—NH_2 \qquad V,$$

wherein $R^6$ is as defined herein before,
to obtain a compound of formula Ic

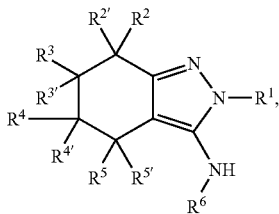

wherein $R^1$ to $R^6$ are as defined herein before, and, if desired, b) transferring the compound of formula Ic into a compound of formula I, wherein $R^7$ is selected from a group consisting of —C(O)—NH—$R^8$, —C(O)—$R^9$, —S(O)$_2$—$R^{10}$ and —C(O)—O$R^{11}$ as defined herein before and, if desired, c) converting the compound obtained into a pharmaceutically acceptable salt.

The nucleophilic aromatic substitution is carried out in a suitable solvent such as for example N,N-dimethylformamide, N,N-dimethylacetamide or N-methyl-2-pyrrolidone at temperatures in the range of ambient temperature to reflux temperature of the solvent.

In more detail, the compounds of formula I can be manufactured by the methods as outlined in schemes A and B below, by the methods given in the examples or by analogous methods. The preparation of compounds of formula I of the present invention may be carried out in sequential or convergent synthetic routes. The substituents and indices used in the following description of the processes have the significance given herein before unless indicated to the contrary. The starting materials are either commercially available, described in the literature or can be prepared by methods well known in the art.

2-Substituted 2H-indazol-3-ylamines and 4,5,6,7-tetrahydro-2H-indazolylamines of formula II are described in the literature, can be prepared by methods well known to a person skilled in the art or by methods described in scheme C and D or in the experimental part. Amines of formula II can be converted to final compounds of the formula Ic by reductive amination with ketones or aldehydes of the formula III, wherein the group CR$^x$R$^y$ corresponds to the $R^6$ group other than phenyl or heteroaryl, using for instance reducing agents like sodium triacetoxyborohydride in the presence of an acid like acetic acid in a solvent like dichloromethane at a temperature ranging from −20° C. to the reflux temperature of the solvent (step a).

Alternatively, amines of formula Ic can be synthesized from 2-substituted 3-chloro-2H-indazoles or 3-chloro-4,5,6,7-tetrahydro-2H-indazoles of the formula IV via nucleophilic aromatic substitution with amines of formula V, e.g. in a solvent like N,N-dimethylformamide, N,N-dimethylacetamide or N-methyl 2-pyrrolidone at temperatures between ambient temperature and the boiling temperature of the solvent (step b). 2-Substituted 3-chloro-2H-indazoles and 3-chloro-4,5,6,7-tetrahydro-2H-indazoles of formula IV are described in the literature, can be prepared by methods well known to a person skilled in the art or by methods described in schemes E and F or in the experimental part.

Scheme A

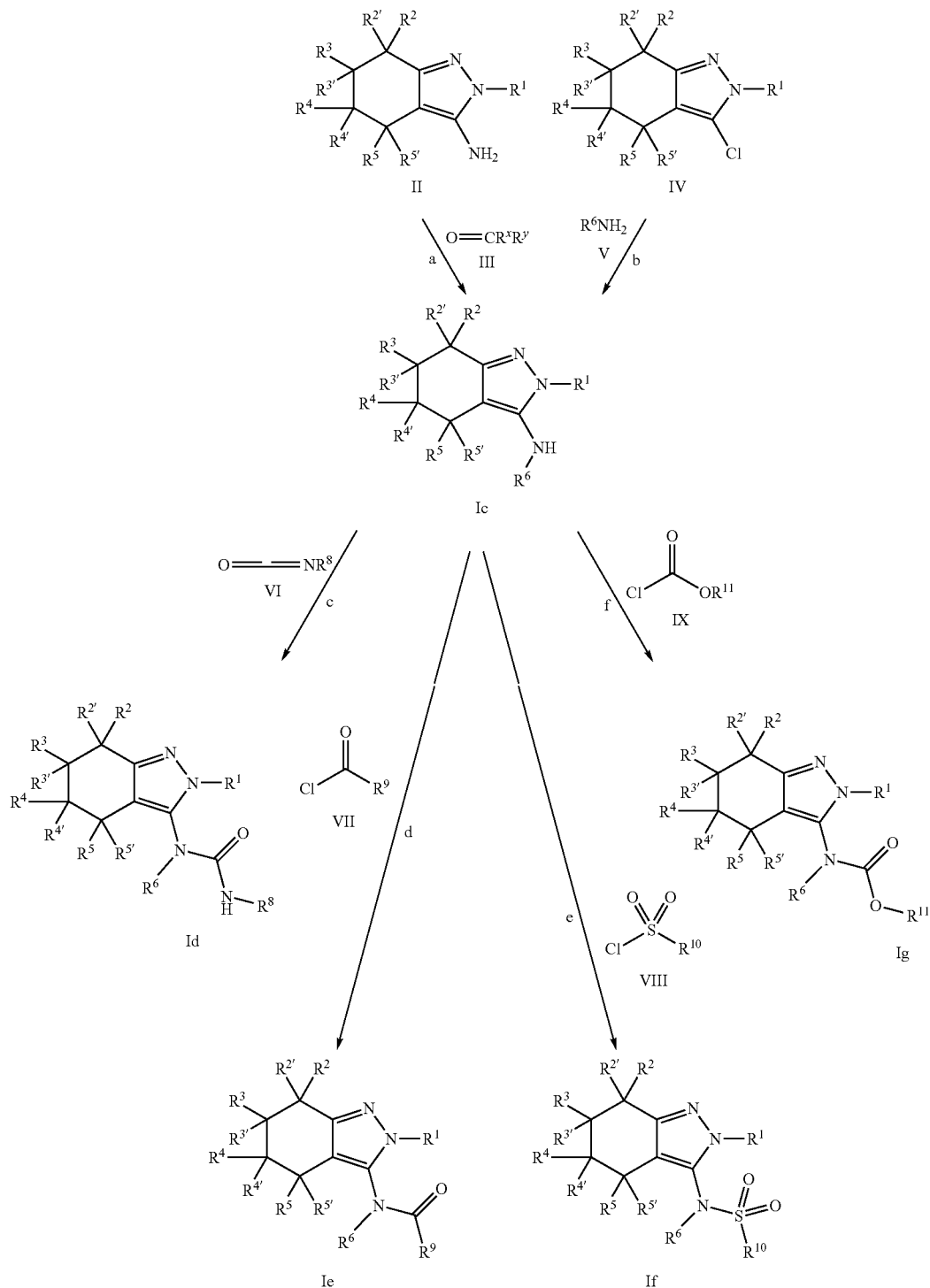

The secondary amines of formula Ic can be further converted to ureas of formula Id by treatment with isocyanides of formula VI, for instance in a solvent like 1,2-dichloroethane or toluene at temperatures ranging from 0° C. to the boiling point of the solvent (step c). Optionally, a base like triethylamine can be added to the reaction mixture. Isocyanides of formula VI are commercially available, described in the literature or can be prepared by methods well known to a person skilled in the art, e.g. by treatment of a corresponding amine $R^8NH_2$ which is either commercially available, described in the literature or can be prepared by methods well known to a person skilled in the art, with triphosgene and triethylamine in a solvent like dichloromethane at temperatures ranging from −20° C. to the reflux temperature of the solvent. Alternatively, amines of formula Ic can be transformed to ureas of formula Id via i) activation of amine of formula Ic with e.g. triphosgene and ii) reaction with an amine $R^8NH_2$.

The amines of formula Ic can further be converted to amides of formula Ie using an activated carboxylic acid derivative like acid chloride of formula VII or by applying other methods known to a person skilled in the art (step d). Amide formation can e.g. be achieved using a base like sodium hydride in a solvent like N,N-dimethylformamide at temperatures between 0° C. and the boiling point of the solvent, preferably at ambient temperature. Activated carboxylic acid derivatives like acid chlorides (VII) are either commercially available, described in the literature or can be prepared by methods well known to a person skilled in the art, e.g. from the corresponding carboxylic acids $R^9COOH$ with thionyl chloride or oxalyl chloride in solvents such as toluene or dichloromethane preferably under reflux conditions. Carboxylic acids $R^9COOH$ are commercially available, described in the literature or can be prepared by methods well known to a person skilled in the art.

In addition, sulfonamides of formula If can be synthesized from the primary amines of formula Ic for instance via treatment of the indazole or 4,5,6,7-tetrahydroindazole of formula Ic and a sulfonyl chloride of formula VIII with a base like sodium hydride in a solvent like N,N-dimethylformamide, preferably at ambient temperature or by other appropriate methods known to a person skilled in the art (step e). Sulfonyl chlorides of formula VIII are commercially available, described in the literature or can be prepared by methods well known to a person skilled in the art.

Carbamates of formula Ig can e.g. be synthesized from the indazoles or 4,5,6,7-tetrahydroindazoles of formula Ic and chloroformates of formula IX using a base like sodium hydride and a solvent like N,N-dimethylformamide, preferably at ambient temperature (step f). Chloroformates of formula IX are described in the literature or can be prepared by methods well known to a person skilled in the art, for instance by treatment of a corresponding alcohol $R^{11}OH$ with triphosgene in a solvent like diethylether preferably at −78° C. Alcohols $R^{11}OH$ are commercially available, described in the literature or can be prepared by methods well known to a person skilled in the art.

Indazoles or 4,5,6,7-tetrahydroindazoles of formulae Id, Ie, If or Ig can contain carboxylic esters which can be hydrolyzed to the corresponding acids using standard procedures, e.g. by treatment with an alkali hydroxide like LiOH or NaOH in a polar solvent mixture like tetrahydrofurane/ethanol/water or by treatment with hydrochloric acid in dioxane in the case of tert-butyl esters. Optionally, indazoles or 4,5,6,7-tetrahydroindazoles of formulae Id, Ie, If or Ig can contain cyano groups which can be converted to the corresponding tetrazoles using standard procedures, e.g. by treatment with sodium azide in the presence of a lewis acid in water or organic solvents like dichloromethane at temperatures between 0° C. and the boiling point of the solvent.

If one of the starting materials, compounds of formulae II to IX, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae II to IX contain chiral centers, indazoles or 4,5,6,7-tetrahydroindazoles of formulae Ic, Id, Ie, If and Ig can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization, e.g. with optically pure amines or by separation of the antipodes by specific chromatographic methods using either a chiral adsorbens or a chiral eluent.

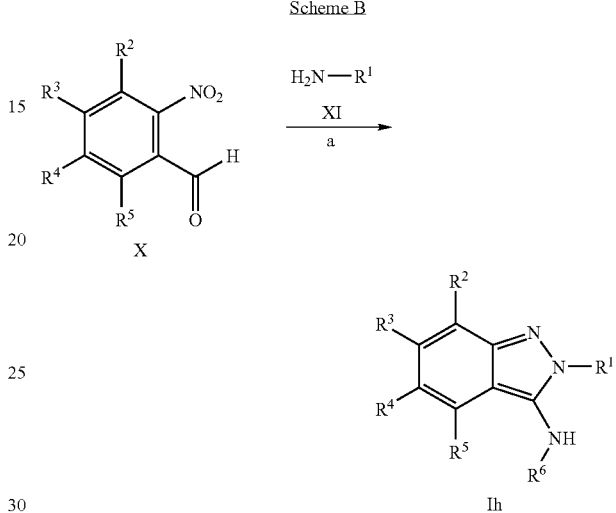

Scheme B

Alternatively, 2H-indazol-3-ylamines of formula Ic (wherein $R^{2'}$ and $R^{3'}$ together as well as $R^{4'}$ and $R^{5'}$ together are replaced by a double bond) can be prepared starting from 2-nitro-benzaldehydes of formula X as described in scheme B or in analogy to the procedure described in G. H. Ahn, J. J. Lee, Y. M. Jun, B. M. Lee, B., H. Kim, Org. Biomol. Chem. 2007, 5, 2472-2485. 2-Nitro-benzaldehydes of formula X are first reacted with primary amines of formula XI in the presence of sodium sulfate in a solvent like tetrahydrofurane preferably at 50° C. to the corresponding imines which are subsequently cyclized to indazoles of formula Ih in the presence of indium and iodine (step a). 2-Nitro-benzaldehydes of formula X and amines of formula XI are commercially available, described in the literature or can be synthesized by methods well known to a person skilled in the art.

If one of the starting materials, compounds of formulae X or XI, contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds of formulae X or XI contain chiral centers, 2H-indazoles of formula Ih can be obtained as mixtures of diastereomers or enantiomers, which can be separated by methods well known in the art, e.g. (chiral) HPLC or crystallization. Racemic compounds can e.g. be separated into their antipodes by separation of the antipodes by specific chromatographic methods using either a chiral adsorbens or a chiral eluent.

Scheme C

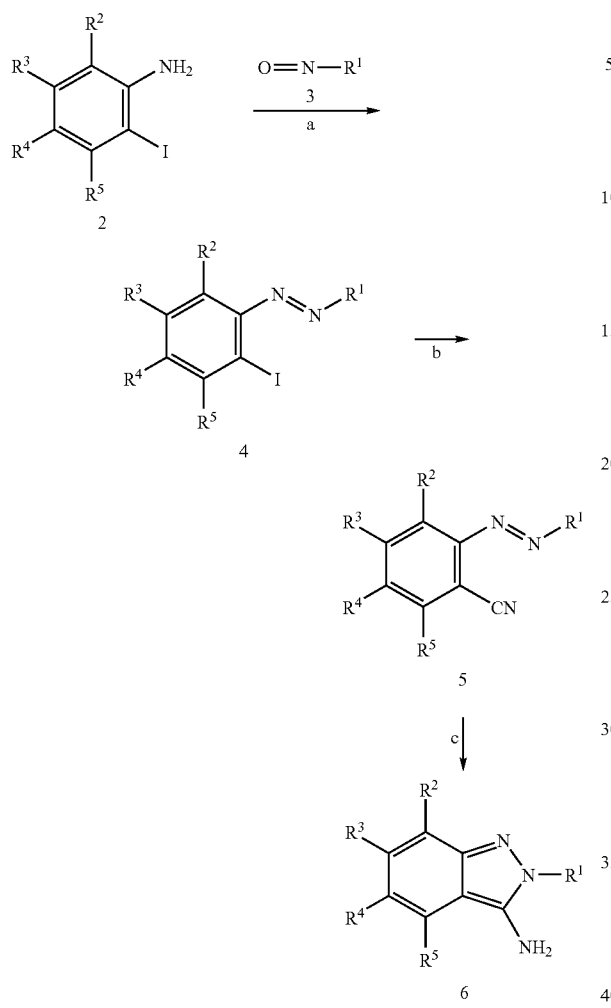

chloride in a solvent like ethanol preferably under reflux conditions leads to 2-substituted 2H-indazol-3-ylamines (6) (step c).

If one of the starting materials, compounds of formula (2) or (3) contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (2) or (3) contain chiral centers, 2-substituted 2H-indazol-3-ylamines (6) can be obtained as mixtures of diastereomers or enantiomers, which can be separated by methods well known in the art, e.g. (chiral) HPLC or crystallization. Racemic compounds can e.g. be separated into their antipodes by separation of the antipodes by specific chromatographic methods using either a chiral adsorbens or a chiral eluent.

Scheme D

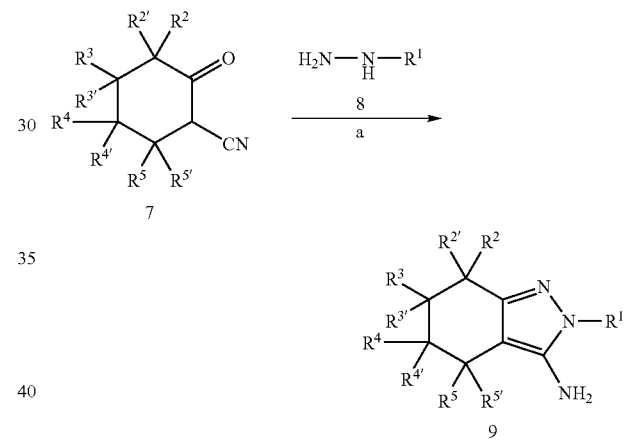

2-Substituted 2H-indazol-3-ylamines (6) (corresponding to compounds of formula II in scheme A) can be prepared starting from 2-iodo-phenylamines (2) as described in scheme C. Optionally, the corresponding 2-bromo-phenylamines can be used instead of 2-iodo-phenylamines (2) as starting materials. 2-Bromo or 2-iodo-phenylamines (2) are commercially available, described in the literature or can be synthesized by methods well known to a person skilled in the art. Treatment of 2-bromo or 2-iodo-phenylamines (2) with nitroso compounds (3) yields 2-bromo or 2-iodo-diazenes (4) (step a). Preferably, these reactions are carried out in a solvent like acetic acid between ambient temperature and the boiling point of the solvent. Nitroso compounds (3) are commercially available, described in the literature or can be synthesized by methods well known to a person skilled in the art, for instance via oxidizing the corresponding amino compounds (which are commercially available or can be synthesized by methods well known to a person skilled in the art) with hydrogen peroxide and molybdenum (VI) oxide in methanol and aqueous potassium hydroxide solution. 2-Bromo or 2-iodo-diazenes (4) can be converted to 2-cyano-diazenes (5), e.g. via treatment with copper (I) cyanide in a solvent like 1-propanol preferably under reflux conditions (step b). Cyclization of 2-cyano-diazenes (5) typically using a reagent like stannous 2-Substituted 4,5,6,7-tetrahydro-2H-indazolylamines (9) (corresponding to compounds of formula II in scheme A) can be prepared from appropriately substituted cyanoketones (7) and arylhydrazines (8) or a salt, e.g. the hydrochloride salt of arylhydrazines (8) as described in scheme D (step a). Preferably, these reactions are carried out in a solvent such as ethanol and the like, at the reflux temperature of the solvent employed. Cyanoketones (7) and arylhydrazines (8) or its corresponding salts are commercially available, described in the literature or can be synthesized by methods well known to a person skilled in the art.

If one of the starting materials, compounds of formula (7) or (8), contains one or more functional groups which are not stable or are reactive under the reaction conditions of the condensation reaction, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (7) or (8) contain chiral centers, 2-substituted 4,5,6,7-tetrahydro-2H-indazolylamines (9) can be obtained as mixtures of diastereomers or enantiomers, which can be separated by methods well known in the art, e.g. (chiral) HPLC or crystallization. Racemic compounds can e.g. be separated into their antipodes by separation of the antipodes by specific chromatographic methods using either a chiral adsorbens or a chiral eluent.

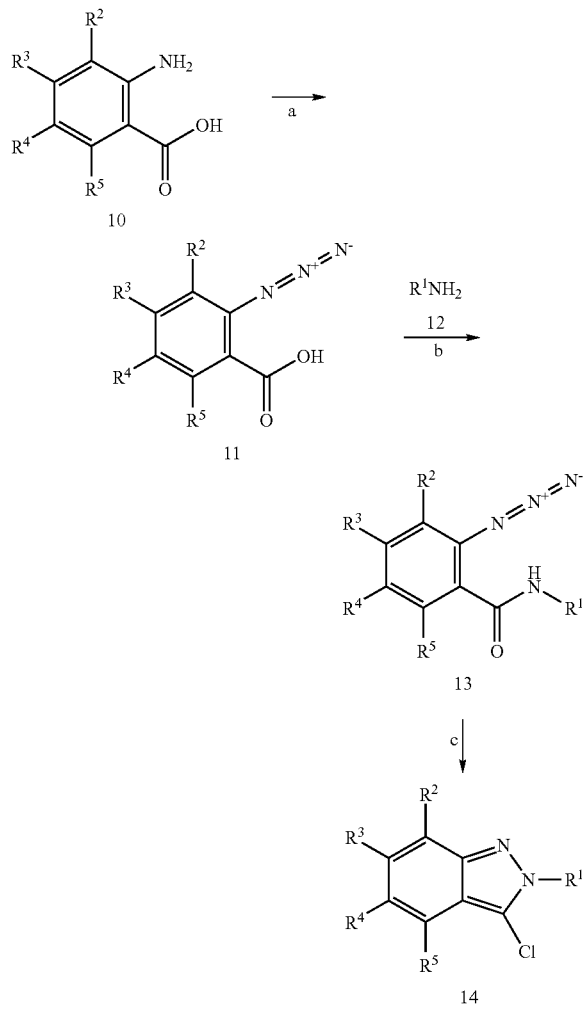

Scheme E

2-Substituted 3-chloro-2H-indazoles (14) (corresponding to compounds of formula IV in scheme A) can be prepared starting from 2-amino-benzoic acids (10) as described in scheme E. 2-Amino-benzoic acids (10) are commercially available, described in the literature or can be synthesized by methods well known to a person skilled in the art. Transformation of amines (10) into 2-azido-benzoic acids (11) can e.g. be achieved via treatment with an aqueous solution of sodium azide preferably at temperatures between −10° C. and ambient temperature (step a). Acids (11) can be condensed—after suitable activation—with amines (12) to amides (13) using standard methods described in the literature (step b). Amines (12) are either commercially available, described in the literature or can be prepared by methods well known to a person skilled in the art. If acid (11) is activated as a carboxylic acid chloride, bromide or carboxylic anhydride the reaction can be performed in a solvent such as dichloromethane, optionally in the presence of a base such as triethylamine, ethyl-diisopropyl-amine or N-ethylmorpholine at temperatures between 0° C. and ambient temperature. Carboxylic acid chlorides can be prepared by methods well known to a person skilled in the art. (e.g. i. carboxylic acid, $CH_2Cl_2$, $(ClCO)_2$, DMF, ambient temperature; or ii. carboxylic acid, thionyl chloride, reflux). Alternatively, carboxylic acids (11) can be in situ activated and transformed into amides (13) using e.g. N-(3-dimethylaminopropyl)-N'-ethyl-carbodiimide-hydrochloride, TBTU (O-(benzotriazol-1-yl)-N,N,N',N'-tetramethyluronium tetrafluoroborate) or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, N,N-dimethylformamide, N,N-dimethylacetamide or dioxane preferably at temperatures between 0° C. and ambient temperature. 2-Azido-amides (13) can for instance be cyclized to 2-substituted 3-chloro-2H-indazoles (14) by boiling them in thionyl chloride (step c).

If one of the starting materials, compounds of formula (10) or (12), contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (10) or (12) contain chiral centers, the 2-substituted 3-chloro-2H-indazoles (14) can be obtained as mixtures of diastereomers or enantiomers, which can be separated by methods well known in the art, e.g. (chiral) HPLC or crystallization. Racemic compounds can e.g. be separated into their antipodes by separation of the antipodes by specific chromatographic methods using either a chiral adsorbens or a chiral eluent.

Scheme F

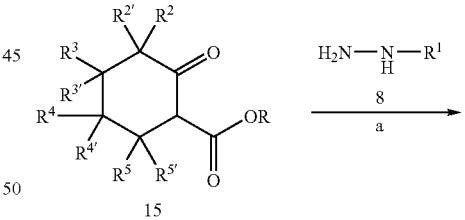

15

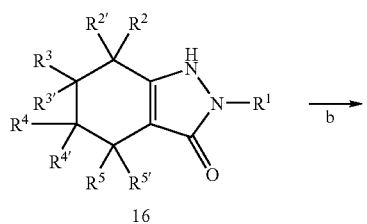

16

-continued

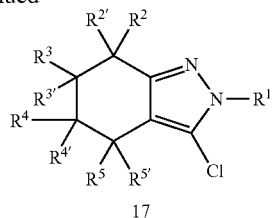

17

2-Substituted 3-chloro-4,5,6,7-tetrahydro-2H-indazoles (17) (corresponding to compounds of formula IV in scheme A) can be prepared starting from cyclohexanone-2-carboxylic acid esters (15) (R is e.g. $C_{1-7}$-alkyl) as described in scheme F. Cyclohexanone-2-carboxylic acid esters (15) are commercially available, described in the literature or can be synthesized by methods well known to a person skilled in the art. Condensation of keto esters (15) with arylhydrazines (8) or a salt e.g. the hydrochloride salt of arylhydrazines (8) gives 2-substituted 1,2,4,5,6,7-hexahydro-indazol-3-ones (16) (step a). Preferably, such condensations are carried out in a solvent such as toluene and the like, at the reflux temperature of the solvent employed. Arylhydrazines (8) or the corresponding arylhydrazine salts are commercially available, described in the literature or can be synthesized by methods well known to a person skilled in the art. 1,2,4,5,6,7-Hexahydro-indazol-3-ones (16) can be converted to 2-substituted 3-chloro-4,5,6,7-tetrahydro-2H-indazoles (17) e.g. by treatment with phosphorus oxychloride in the presence of catalytic amounts of N,N-dimethyl-aniline, preferably under reflux conditions (step b).

If one of the starting materials, compounds of formula (15) or (8), contains one or more functional groups which are not stable or are reactive under the reaction conditions of one or more reaction steps, appropriate protecting groups (PG) (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (15) or (8) contain chiral centers, 2-substituted 3-chloro-4,5,6,7-tetrahydro-2H-indazoles (17) can be obtained as mixtures of diastereomers or enantiomers, which can be separated by methods well known in the art, e.g. (chiral) HPLC or crystallization. Racemic compounds can e.g. be separated into their antipodes by separation of the antipodes by specific chromatographic methods using either a chiral adsorbens or a chiral eluent.

As described above, the novel compounds of the present invention have been found to bind to and selectively activate FXR. They can therefore be used in the treatment or prophylaxis of diseases and conditions that are affected by FXR modulators. Preferably, the FXR modulators are FXR agonists.

"Diseases which are affected by FXR modulators" include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease. Preferred diseases (and conditions) which are affected by FXR modulators are prevention or treatment of high LDL cholesterol levels, high triglycerides, dyslipidemia, cholesterol gallstone disease, cancer, non-insulin dependent diabetes mellitus and metabolic syndrome. Particularly preferred diseases which are affected by FXR modulators are high LDL cholesterol, high triglyceride levels and dyslipidemia.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment or prophylaxis of diseases which are affected by FXR modulators, particularly as therapeutically active substances for the treatment or prophylaxis of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

In another preferred embodiment, the invention relates to a method for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease, which method comprises administering a compound as defined above to a human being or animal.

The invention also embraces the use of compounds as defined above for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease.

The invention also relates to the use of compounds as described above for the preparation of medicaments for the therapeutic or prophylactic treatment of diseases which are affected by FXR modulators, particularly for the therapeutic or prophylactic treatment of increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and Alzheimer's disease. Such medicaments comprise a compound as described above.

Also contemplated herein is a combination therapy using one or more compounds of formula I or compositions provided herein, or a pharmaceutically acceptable derivative thereof, in combination with one or more compounds selected from the group consisting of the following: cholesterol biosynthesis inhibitors (HMG CoA reductase inhibitors, e.g. lovastatin, simvastatin, pravastatin, fluvastatin, atorvastatin, cerivastatin, nisvastatin and rivastatin); squalene epoxidase inhibitors (e.g. terbinafine); plasma HDL-raising agents (e.g. CETP inhibitors e.g. anacetrapib, R1658); human peroxisome proliferator activated receptor (PPAR) gamma agonists (e.g. thiazolidinediones e.g. rosiglitazone, troglitazone, and pioglitazone); PPAR alpha agonists (e.g. clofibrate, fenofibrate and gemfibronzil); PPAR dual alpha/gamma agonists (e.g. muraglitazar, aleglitazar, peliglitazar); bile acid sequestrants (e.g. anion exchange resins, or quaternary amines (e.g. cholestyramine or colestipol)); bile acid transport inhibitors (BATi); nicotinic acid, niacinamide; cholesterol absorption inhibitors (e.g. ezetimibe); acyl-Coenzyme A:cholesterol O-acyl transferase (ACAT) inhibitors (e.g. avasimibe); selective estrogen receptor modulators (e.g. raloxifene or tamoxifen); LXR alpha or beta agonists, antagonists or partial agonists (e.g. 22(R)-hydroxycholesterol, 24(S)-hydroxycholesterol, T0901317 or GW3965); microsomal triglyceride transfer protein (MTP) inhibitors, anti-diabetes agents such as, e.g. insulin and insulin analogs (e.g. LysPro insulin, inhaled formulations comprising insulin; sulfonylureas and analogues (e.g. tolazamide, chlorpropamide, glipizide, glimepiride, glyburide, glibenclamide, tolbutamide, acetohexamide, glypizide), biguanides (e.g. metformin or metformin hydrochloride, phenformin, buformin) alpha2-antagonists and imidazolines (e.g. midaglizole, isaglidole, deriglidole, idazoxan, efaroxan, fluparoxan), thiazolidinediones (e.g. pioglitazone hydrochloride, rosiglitazone maleate, ciglitazone, troglitazone or balaglitazone), alpha-glucosidase inhibitors (e.g. miglitol, acarbose, epalrestat, or voglibose), meglitinides (e.g. repaglinide or nateglinide), DPP-4 inhibitors (e.g. sitagliptin phosphate, saxagliptin, vildagliptin, alogliptin or denagliptin), incretins (e.g. glucagon-like peptide-1 (GLP-1) receptor agonists (e.g. Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™ and glucose-dependent insulinotropic peptide (GIP)); amylin agonists (e.g. pramlintide, AC-137); insulin secretagogues (e.g. linogliride, nateglinide, repaglinide, mitiglinide calcium hydrate or meglitinide); SGLT-2 inhibitors (e.g. dapagliflozin (BMS), sergliflozin (Kissei), AVE 2268 (Sanofi-Aventis); Glucokinase activators such as the compounds disclosed in e.g. WO 00/58293 A1; anti-obesity agents such as nerve growth factor agonist (e.g. axokine), growth hormone agonists (e.g. AOD-9604), adrenergic uptake inhibitors (e.g. GW-320659), 5-HT (serotonin) reuptake/transporter inhibitors (e.g. Prozac), 5-HT/NA (serotonin/noradrenaline) reuptake inhibitors (e.g. sibutramine), DA (dopamine) reuptake inhibitors (e.g. Buprobrion), 5-HT, NA and DA reuptake blockers, steroidal plant extracts (e.g. P57), NPY1 or 5 (neuropeptide Y Y1 or Y5) antagonists, NPY2 (neuropeptide Y Y2) agonists, MC4 (melanocortin 4) agonists, CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g. SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, 5-$HT_{2C}$ (serotonin receptor 2C) agonists (e.g. Lorcaserin), PDE (phosphodiesterase) inhibitors, fatty acid transporter inhibitors, dicarboxylate transporter inhibitors, glucose transporter inhibitors, CB-1 (cannabinoid-1 receptor) inverse agonists or antagonists (e.g. SR141716), lipase inhibitors (e.g. orlistat); cyclooxygenase-2 (COX-2) inhibitors (e.g. rofecoxib and celecoxib); thrombin inhibitors (e.g. heparin, argatroban, melagatran, dabigatran); platelet aggregation inhibitors (e.g. glycoprotein IIb/IIIa fibrinogen receptor antagonists or aspirin); vitamin B6 and pharmaceutically acceptable salts thereof; vitamin B 12; folic acid or a pharmaceutically acceptable salt or ester thereof; antioxidant vitamins such as C and E and beta carotene; beta blockers (e.g. angiotensin II receptor antagonists such as losartan, irbesartan or valsartan; antiotensin converting enzyme inhibitors such as enalapril and captopril; calcium channel blockers such as nifedipine and diltiazam; endothelian antagonists; aspirin; agents other than LXR ligands that enhance ATP-Binding Cassette Transporter-Al gene expression; and bisphosphonate compounds (e.g. alendronate sodium).

The following tests were carried out in order to determine the activity of the compounds of formula I. Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in E. coli strain BL21(pLysS) cells by standard methods (Current Protocols in Molecular Biology, Wiley Press, ed. Ausubel et al).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$. For each reaction well in a 96-well plate, 40 nM of GST-FXR LBD fusion protein was bound to 10 μg glutathione ytrium silicate SPA beads (Pharmacia Amersham) in a final volume of 50 μl by shaking. A radioligand (e.g. 40 nM) of 2,N-dicyclohexyl-2-

[2-(2,4 dimethoxy-phenyl)-benzoimidazol-1-yl]-acetamide) was added, and the reaction incubated at RT for 30 minutes in the presence of test compounds followed by scintillation proximity counting. All binding assays were performed in 96-well plates and the amount of bound ligand was measured on a Packard TopCount using OptiPlates (Packard). Dose response curves were performed within a range of concentration from $6 \times 10^{-9}$ M to $2.5 \times 10^{-5}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plates at a density of $10^5$ cells/well and then transfected with the pFA-FXR-LBD or expression plasmid plus a reporter plasmid. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula I have an activity in at least one of the above assays ($EC_{50}$ or $IC_{50}$), preferably in the range of 0.5 nM to 10 μM, more preferably 0.5 nM to 100 nM.

For example, compounds of formula I of the present invention showed the following $IC_{50}$ values in the binding assay described above:

| Example | $IC_{50}$ [μM] |
|---|---|
| 1 | 0.04 |
| 3 | 0.83 |
| 4 | 0.18 |
| 9 | 1.08 |
| 10 | 0.66 |
| 11 | 0.02 |
| 12 | 0.79 |
| 15 | 0.46 |
| 16 | 0.40 |
| 17 | 2.33 |
| 19 | 0.02 |
| 21 | 0.72 |
| 25 | 0.79 |
| 26 | 0.34 |
| 28 | 0.07 |
| 31 | 4.31 |
| 32 | 3.35 |
| 35 | 0.02 |
| 37 | 0.06 |
| 38 | 0.24 |
| 40 | 0.02 |
| 41 | 0.30 |
| 43 | 0.08 |
| 44 | 0.10 |

The compounds of formula I and their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

Abbreviations $CH_2Cl_2$=dichloromethane, $CH_3CN$=acetonitrile, d=day, DMF=N,N-dimethylformamide, eq.=equivalent(s), $Et_3N$=triethylamin, EtOAc=ethyl acetate, h=hour, HCl=hydrochloric acid, iPrOAc=isoproyl acetate, MeOH=methanol, min=minutes, NaH=sodium hydride, NaHCO₃=sodium bicarbonate, NaOH=sodium hydroxide, Na₂SO₄=sodium sulfate, quant.=quantitative, TBME=tert-butylmethyl ether, THF=tetrahydrofuran.

Example 1

1,3-Dicyclohexyl-1-(2-phenyl-2H-indazol-3-yl)-urea

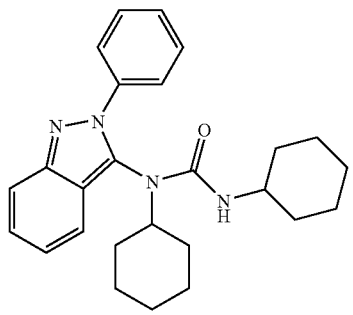

1.1 Cyclohexyl-(2-phenyl-2H-indazol-3-yl)-amine

To a solution of 2-phenyl-2H-indazol-3-amine (800 mg, 4 mmol; Shirtcliff, Laura D.; Rivers, Jazmin; Haley, Michael M, Journal of Organic Chemistry (2006), 71(17), 6619-6622) in CH₂Cl₂ (43 ml) was added cyclohexanone (1.97 ml, 19 mmol; [108-94-1]), acetic acid (0.22 ml, 4 mmol) and sodium triacetoxyborohydride (2.43 g, 11 mmol) at ambient temperature under an argon atmosphere. The reaction mixture was heated under reflux conditions for 12 h, poured onto ice water/aqueous NaHCO₃ solution 1/1 and extracted two times with CH₂Cl₂. The combined extracts were washed with ice water/brine 1/1 and dried over Na₂SO₄. After filtration the solvent was removed under reduced pressure, the resulting brown oil was dissolved in MeOH (20 ml) and heated under reflux conditions for 30 min. Removal of the solvent under reduced pressure left a brown oil which was purified by column chromatography (silica gel, iPrOAc/heptane) to give the title compound (206 mg, 0.7 mmol; 18%) as yellow oil. MS: m/e=292.4 [M+H⁺].

1.2 1,3-Dicyclohexyl-1-(2-phenyl-2H-indazol-3-yl)-urea

Cyclohexylisocyanate (13 ul, 0.1 mmol; [3173-53-3]) was added at ambient temperature to a solution of cyclohexyl-(2-phenyl-2H-indazol-3-yl)-amine (30 mg, 0.1 mmol) in toluene (0.4 ml) under an argon atmosphere. The solution was heated under reflux conditions for 12 h, cyclohexylisocyanate (7 μl, 60 μmol; [3173-53-3]) was added and heating was continued for further 6 h. The solvent was removed under reduced pressure to give a brown oil which was purified by preparative thin layer chromatography (silica gel, iPrOAc/heptane) to give the title compound (11 mg, 26 μmol; 27%) as off-white solid. MS: m/e=417.4 [M+H⁺].

Example 2

4-[3-Cyclohexyl-3-(2-phenyl-2H-indazol-3-yl)-ureido]-benzoic acid

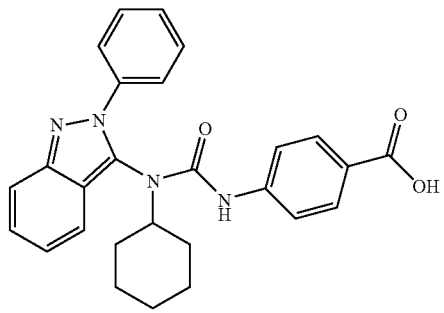

2.1 4-[3-Cyclohexyl-3-(2-phenyl-2H-indazol-3-yl)-ureido]-benzoic acid ethyl ester In analogy to the procedure described in example 1.2, cyclohexyl-(2-phenyl-2H-indazol-3-yl)-amine (example 1.1) was reacted with 4-isocyanato-benzoic acid ethyl ester ([30806-83-8]) in toluene to give the title compound as yellow solid. MS: m/e=483.3 [M+H⁺].

2.2 4-[3-Cyclohexyl-3-(2-phenyl-2H-indazol-3-yl)-ureido]-benzoic acid

To a solution of 4-[3-cyclohexyl-3-(2-phenyl-2H-indazol-3-yl)-ureido]-benzoic acid ethyl ester (10 mg, 21 μmol in THF/MeOH 2/1 (150 μl) was a added a 1 N aqueous lithium hydroxide solution (120 μl, 120 μmmol) at ambient temperature under an argon atmosphere. The reaction mixture was stirred for 12 h at ambient temperature, poured onto ice water/1 N aqueous HCl solution 1/1 and extracted two times with iPrOAc. The combined extracts were washed with ice water/brine 1/1 and dried over Na₂SO₄. After filtration the solvent was removed under reduced pressure to give the title compound (10 mg, 22 umol; quant.) as yellow solid. MS: m/e=455.4 [M+H⁺].

Example 3

1-Cyclohexyl-3-(2-fluoro-phenyl)-1-(2-phenyl-2H-indazol-3-yl)-urea

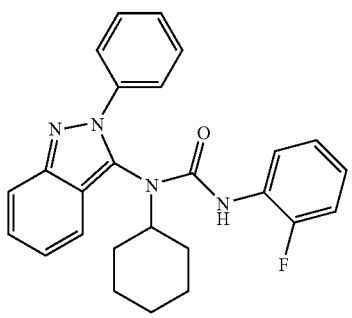

In analogy to the procedure described in example 1.2, cyclohexyl-(2-phenyl-2H-indazol-3-yl)-amine (example 1.1) was reacted with 1-fluoro-2-isocyanato-benzene ([16744-98-2]) in toluene for 48 h under reflux conditions to give the title compound as colorless oil. MS: m/e=429.5 [M+H⁺].

Example 4

1-Butyl-1-[2-(4-chloro-phenyl)-2H-indazol-3-yl]-3-cyclohexyl-urea

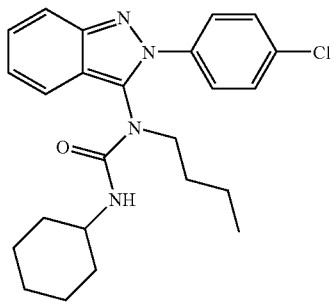

4.1 Butyl-[2-(4-chloro-phenyl)-2H-indazol-3-yl]-amine

A solution of 3-chloro-2-(4-chloro-phenyl)-2H-indazole (30 mg, 137 umol; Ardakani, Manouchehr; Smalley, Robert K.; Smith, Richard H., Synthesis (1979), (4), 308-9) and n-butylamine (230 µl, 2.3 mmol) in N-methyl 2-pyrrolidone (0.4 ml) in a sealed tube was heated for 48 h to 175° C. The reaction mixture was poured onto ice water/brine 1/1 and extracted two times with iPrOAc. The combined extracts were washed with ice water/brine 1/1 and dried over Na₂SO₄. After filtration the solvent was removed under reduced pressure to give a brown oil which was purified by preparative thin layer chromatography (silica gel, iPrOAc/heptane) to give the title compound (11 mg, 37 umol; 32%) as yellow solid. MS: m/e=300.1 [M+H⁺].

4.2 1-Butyl-1-[2-(4-chloro-phenyl)-2H-indazol-3-yl]-3-cyclohexyl-urea

In analogy to the procedure described in example 1.2, butyl-[2-(4-chloro-phenyl)-2H-indazol-3-yl]-amine was reacted with cyclohexylisocyanate ([3173-53-3]) to give the title compound as yellow solid. MS: m/e=425.3 [M+H⁺].

Example 5

1-Cyclohexyl-3-(2,6-dimethyl-phenyl)-1-(2-phenyl-2H-indazol-3-yl)-urea

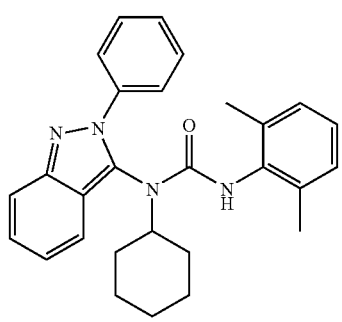

In analogy to the procedure described in example 1.2, cyclohexyl-(2-phenyl-2H-indazol-3-yl)-amine (example 1.1) was reacted with 2-isocyanato-1,3-dimethyl-benzene ([28556-81-2]) in toluene for 72 h under reflux conditions to give the title compound as yellow oil. MS: m/e=439.3 [M+H⁺].

Example 6

Benzyl-(2-phenyl-2H-indazol-3-yl)-amine

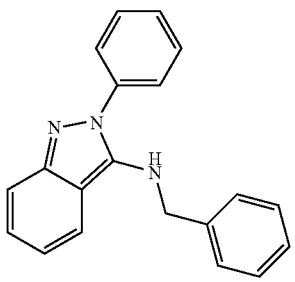

6.1 (2-Phenyl-2H-indazol-3-yl)-[1-phenyl-methylidene]-amine

To a solution of 2-phenyl-2H-indazol-3-amine (300 mg, 1.4 mmol; Shirtcliff, Laura D.; Rivers, Jazmin; Haley, Michael M, Journal of Organic Chemistry (2006), 71(17), 6619-6622) in CH₂Cl₂ (16 ml) was added benzaldehyde (730 µl, 7.2 mmol; [100-52-7]), acetic acid (220 ul, 4.3 mmol) and sodium triacetoxyborohydride (912 mg, 4.3 mmol) at ambient temperature under an argon atmosphere. The reaction mixture was heated under reflux conditions for 64 h, poured onto ice water/aqueous NaHCO₃ solution 1/1 and extracted two times with CH₂Cl₂. The combined extracts were washed with ice water/brine 1/1 and dried over Na₂SO₄. After filtration the solvent was removed under reduced pressure, the resulting yellow oil was purified by column chromatography (silica gel, iPrOAc/heptane) to give the title compound (470 mg, 1.5 mmol; quant.) as yellow solid. MS: m/e=298.1 [M+H⁺].

6.2 Benzyl-(2-phenyl-2H-indazol-3-yl)-amine

Sodium borohydride (245 mg, 6.46 mmol) was added to a suspension of (2-phenyl-2H-indazol-3-yl)-[1-phenyl-methylidene]-amine (480 mg, 1.61 mmol) in ethanol (13 ml) at ambient temperature under an argon atmosphere. The reaction mixture was stirred at ambient temperature for 12 h, poured onto ice water/aqueous NaHCO₃ solution 1/1 and extracted two times with iPrOAc. The combined extracts were washed with ice water/brine 1/1 and dried over Na₂SO₄. After filtration the solvent was removed under reduced pressure, the resulting yellow oil was purified by column chromatography (silica gel, iPrOAc/heptane) to give the title compound (314 mg, 1.05 mmol; 65%) as yellow oil. MS: m/e=300.4 [M+H$^+$].

Example 7

1-Benzyl-1-[2-(4-chloro-phenyl)-2H-indazol-3-yl]-3-cyclohexyl-urea

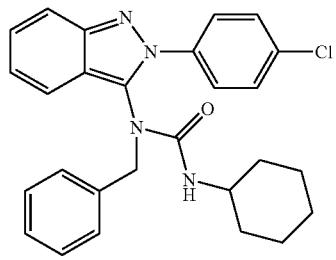

7.1 Benzyl-[2-(4-chloro-phenyl)-2H-indazol-3-yl]-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with benzylamine in N-methyl 2-pyrrolidone for 48 h at 175° C. in a sealed tube to give the title compound as yellow oil. MS: m/e=334.4 [M+H$^+$].

7.2 1-Benzyl-1-[2-(4-chloro-phenyl)-2H-indazol-3-yl]-3-cyclohexyl-urea

In analogy to the procedure described in example 1.2, benzyl-[2-(4-chloro-phenyl)-2H-indazol-3-yl]-amine was reacted with cyclohexylisocyanate ([3173-53-3]) in toluene for 48 h under reflux conditions to give the title compound as yellow solid. MS: m/e=459.4 [M+H$^+$].

Example 8

3-[3-Cyclohexyl-3-(2-phenyl-2H-indazol-3-yl)-ureido]-benzoic acid

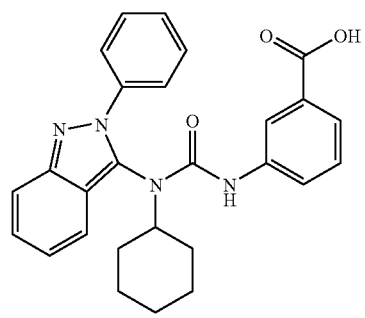

8.1 3-[3-Cyclohexyl-3-(2-phenyl-2H-indazol-3-yl)-ureido]-benzoic acid methyl ester In analogy to the procedure described in example 1.2, cyclohexyl-(2-phenyl-2H-indazol-3-yl)-amine (example 1.1) was reacted with 3-isocyanato-benzoic acid ethyl ester ([41221-47-0]) in toluene for 72 h under reflux conditions to give the title compound as yellow oil. MS: m/e=469.3 [M+H$^+$].

8.2 3-[3-Cyclohexyl-3-(2-phenyl-2H-indazol-3-yl)-ureido]-benzoic acid

In analogy to the procedure described in example 2.2, 3-[3-cyclohexyl-3-(2-phenyl-2H-indazol-3-yl)-ureido]-benzoic acid methyl ester was treated with 1 N aqueous lithium hydroxide solution in THF/MeOH 1/1 for 5 h at ambient temperature to give the title compound as yellow foam. MS: m/e=455.1 [M+H$^+$].

Example 9

4-{3-Benzyl-3-[2-(4-chloro-phenyl)-2H-indazol-3-yl]-ureido}-3-chloro-benzoic acid

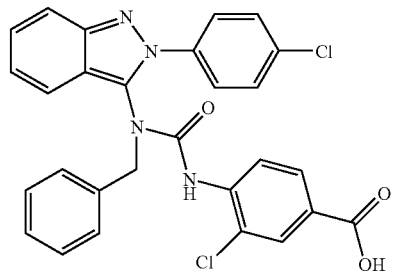

9.1 3-Chloro-4-isocyanato-benzoic acid methyl ester

To an ice cold solution of triphosgene (59 mg, 200 µmol) in CH$_2$Cl$_2$ (1.5 ml) was added 4-amino-3-chloro-benzoic acid methyl ester (100 mg, 540 µmol; [84228-44-4]) and a solution of Et$_3$N (150 µl, 1.1 mmol) in CH$_2$Cl$_2$ (0.5 ml) under an argon atmosphere. The reaction mixture was stirred at ambient temperature for 30 min. The solvent was removed under reduced pressure. The residue was triturated with EtOAc, the solid was filtered off and the filtrate was evaporated to dryness under reduced pressure to give the title compound (111 mg, 520 µmol; 97%) as brown solid which was used in the next step without further purification. MS: m/e=228.9 [M+H$^+$].

9.2 4-{3-Benzyl-3-[2-(4-chloro-phenyl)-2H-indazol-3-yl]-ureido}-3-chloro-benzoic acid methyl ester In analogy to the procedure described in example 1.2, benzyl-[2-(4-chloro-phenyl)-2H-indazol-3-yl]-amine (example 7.1) was reacted with 3-chloro-4-isocyanato-benzoic acid methyl ester in toluene for 72 h under reflux conditions to give the title compound as yellow oil. MS: m/e=547.0 [M+H$^+$].

9.3 4-{3-Benzyl-3-[2-(4-chloro-phenyl)-2H-indazol-3-yl]-ureido}-3-chloro-benzoic acid In analogy to the procedure described in example 2.2, 4-{3-benzyl-3-[2-(4-chloro-phenyl)-2H-indazol-3-yl]-ureido}-3-chloro-benzoic acid methyl ester was treated with 1 N aqueous lithium hydroxide solution in THF/MeOH 1/1 for 3 days at ambient temperature to give the title compound as colorless oil. MS: m/e=530.0 [M−H⁻].

Example 10

1-[2-(4-Chloro-phenyl)-2H-indazol-3-yl]-3-cyclohexyl-1-(tetrahydro-pyran-4-yl)-urea

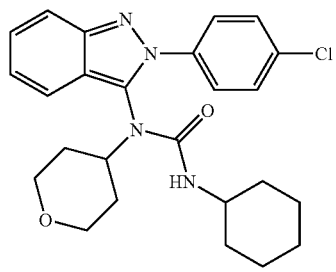

10.1 [2-(4-Chloro-phenyl)-2H-indazol-3-yl]-(tetrahydro-pyran-4-yl)-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with tetrahydro-pyran-4-ylamine ([38041-19-9]) in N-methyl 2-pyrrolidone for 48 h at 175° C. in a sealed tube to give the title compound as yellow solid. MS: m/e=328.4 [M+H⁺].

10.2 1-[2-(4-Chloro-phenyl)-2H-indazol-3-yl]-3-cyclohexyl-1-(tetrahydro-pyran-4-yl)-urea In analogy to the procedure described in example 1.2, [2-(4-chloro-phenyl)-2H-indazol-3-yl]-(tetrahydro-pyran-4-yl)-amine was reacted with cyclohexylisocyanate ([3173-53-3]) in toluene for 5 days under reflux conditions to give the title compound as yellow oil. MS: m/e=453.3 [M+H⁺].

Example 11

1-[2-(4-Chloro-phenyl)-2H-indazol-3-yl]-1,3-dicyclohexyl-urea

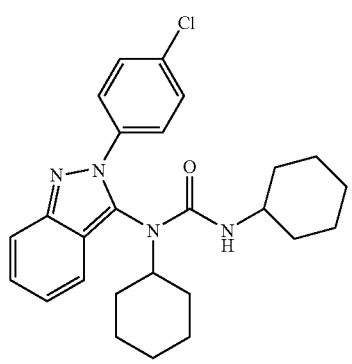

11.1 [2-(4-Chloro-phenyl)-2H-indazol-3-yl]cyclohexyl-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with cyclohexylamine ([108-91-8]) in N-methyl 2-pyrrolidone for 48 h at 175° C. in a sealed tube to give the title compound as brown oil. MS: m/e=327.3 [M+H⁺].

11.2 1-[2-(4-Chloro-phenyl)-2H-indazol-3-yl]-1,3-dicyclohexyl-urea

In analogy to the procedure described in example 1.2, [2-(4-chloro-phenyl)-2H-indazol-3-yl]-cyclohexyl-amine was reacted with cyclohexylisocyanate ([3173-53-3]) in toluene for 24 h under reflux conditions to give the title compound as yellow oil. MS: m/e=451.1 [M+H⁺].

Example 12

4-{3-Butyl-3-[2-(4-chloro-phenyl)-2H-indazol-3-yl]-ureido}-3-chloro-benzoic acid

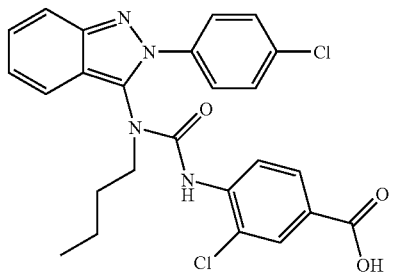

12.1 4-{3-Butyl-3-[2-(4-chloro-phenyl)-2H-indazol-3-yl]-ureido}-3-chloro-benzoic acid methyl ester In analogy to the procedure described in example 1.2, butyl-[2-(4-chloro-phenyl)-2H-indazol-3-yl]-amine (example 4.1) was reacted with 3-chloro-4-isocyanato-benzoic acid methyl ester (example 9.1) in toluene for 5 d under reflux conditions to give the title compound as colorless foam. MS: m/e=510.9 [M+H⁺].

12.2 4-{3-Butyl-3-[2-(4-chloro-phenyl)-2H-indazol-3-yl]-ureido}-3-chloro-benzoic acid In analogy to the procedure described in example 2.2, 4-{3-butyl-3-[2-(4-chloro-phenyl)-2H-indazol-3-yl]-ureido}-3-chloro-benzoic acid methyl ester was treated with 1 N aqueous lithium hydroxide solution in THF/MeOH 1/1 for 14 h at ambient temperature to give the title compound as colorless foam. MS: m/e=496.1 [M–H⁻].

Example 13

4-[3-Cyclohexyl-3-(2-phenyl-2H-indazol-3-yl)-ureido]-3-methyl-benzoic acid

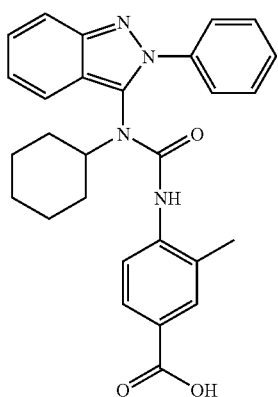

13.1 3-Methyl-4-isocyanato-benzoic acid methyl ester

In analogy to the procedure described in example 9.1, 4-amino-3-methyl-benzoic acid methyl ester ([18595-14-7]) was reacted with triphosgene in the presence of Et₃N in CH₂Cl₂ under reflux conditions for 14 h to give the title compound as brown solid. MS: m/e=191.1 [M⁺].

13.2 4-[3-Cyclohexyl-3-(2-phenyl-2H-indazol-3-yl)-ureido]-3-methyl-benzoic acid methyl ester In analogy to the procedure described in example 1.2, cyclohexyl-(2-phenyl-2H-indazol-3-yl)-amine (example 1.1) was reacted with 3-methyl-4-isocyanato-benzoic acid methyl ester in toluene for 4 d under reflux conditions to give the title compound as white solid. MS: m/e=483.4 [M+H⁺].

13.3 4-[3-Cyclohexyl-3-(2-phenyl-2H-indazol-3-yl)-ureido]-3-methyl-benzoic acid In analogy to the procedure described in example 2.2, 4-[3-cyclohexyl-3-(2-phenyl-2H-indazol-3-yl)-ureido]-3-methyl-benzoic acid methyl ester was treated with 1 N aqueous lithium hydroxide solution in THF/MeOH 1/1 for 14 h at ambient temperature to give the title compound as off-white solid. MS: m/e=469.4 [M+H⁺].

Example 14

3-Chloro-4-[3-cyclohexyl-3-(2-phenyl-2H-indazol-3-yl)-ureido]-benzoic acid

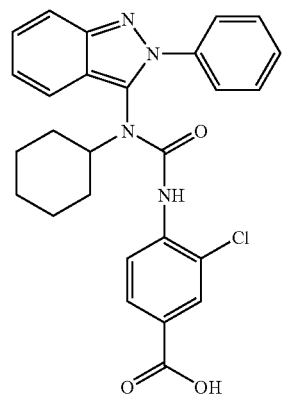

14.1 3-Chloro-4-[3-cyclohexyl-3-(2-phenyl-2H-indazol-3-yl)-ureido]-benzoic acid methyl ester In analogy to the procedure described in example 1.2, cyclohexyl-(2-phenyl-2H-indazol-3-yl)-amine (example 1.1) was reacted with 3-chloro-4-isocyanato-benzoic acid methyl ester (example 9.1) in toluene for 4 days under reflux conditions to give the title compound as white solid. MS: m/e=503.0 [M+H⁺].

14.2 3-Chloro-4-[3-cyclohexyl-3-(2-phenyl-2H-indazol-3-yl)-ureido]-benzoic acid In analogy to the procedure described in example 2.2, 3-chloro-4-[3-cyclohexyl-3-(2-phenyl-2H-indazol-3-yl)-ureido]-benzoic acid methyl ester was treated with 1 N aqueous lithium hydroxide solution in THF/MeOH 1/1 for 16 h at ambient temperature to give the title compound as off-white solid. MS: m/e=489.3 [M+H⁺].

Example 15

1-[2-(4-Chloro-phenyl)-2H-indazol-3-yl]-3-cyclohexyl-1-phenyl-urea

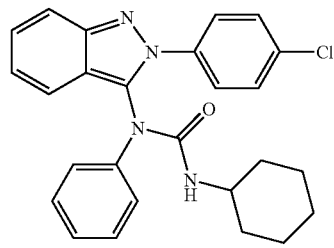

15.1 [2-(4-Chloro-phenyl)-2H-indazol-3-yl]-phenyl-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with phenylamine ([62-53-3]) in N-methyl 2-pyrrolidone for 48 h at 175° C. in a sealed tube to give the title compound as brown solid. MS: m/e=320.1 [M+H$^+$].

15.2 1-[2-(4-Chloro-phenyl)-2H-indazol-3-yl]-3-cyclohexyl-1-phenyl-urea

In analogy to the procedure described in example 1.2, [2-(4-chloro-phenyl)-2H-indazol-3-yl]-phenyl-amine was reacted with cyclohexylisocyanate ([3173-53-3]) in toluene for 5 days under reflux conditions to give the title compound as yellow oil. MS: m/e=445.1 [M+H$^+$].

Example 16

3-Chloro-4-{3-[2-(4-chloro-phenyl)-5,6-difluoro-2H-indazol-3-yl]-3-cyclohexyl-ureido}-benzoic acid

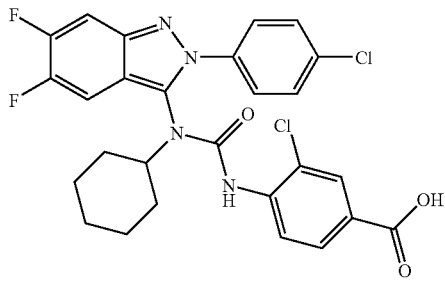

16.1 (4-Chloro-phenyl)-(4,5-difluoro-2-iodo-phenyl)-diazene

Chloro-4-nitroso-benzene (9.1 g, 64 mmol; [932-98-9]) was added to a solution of 4,5-difluoro-2-iodo-phenylamine (10.9 g, 43 mmol; [847685-01-2]) in acetic acid (430 ml). The reaction mixture was heated under reflux conditions for 14 h. Ice water (1 l) and EtOAc (1 l) was added, the layers were separated and the aqueous layer was extracted two times with EtOAc. The combined extracts were washed with water and brine and dried over Na$_2$SO$_4$. The solvent was removed under reduced pressure and the residue was purified by column chromatography (silica gel, CH$_2$Cl$_2$/heptane) to give the title compound (4.34 g, 11 mmol; 27%) as orange solid. MS: m/e=377.9 [M$^+$].

16.2 2-(4-chloro-phenylazo)-4,5-difluoro-benzonitrile

Copper (I) cyanide (9.76 g, 109 mmol) was added to a solution of (4-chloro-phenyl)-(4,5-difluoro-2-iodo-phenyl)-diazene (5.89 g, 16 mmol) in 1-propanol (95 ml) under an argon atmosphere. The reaction mixture was heated under reflux conditions for 14 h and diluted with CH$_2$Cl$_2$/heptane 1/1 (70 ml). The suspension was filtered and the filtrate was evaporated to dryness to give the title compound (3.3 g, 12 mmol; 77%) as brown solid which was used in the next step without further purification. MS: m/e=278.0 [M+H$^+$].

16.3 2-(4-Chloro-phenyl)-5,6-difluoro-2H-indazol-3-ylamine

Tin(II) chloride (11.4 g, 60 mmol) was added to a solution of 2-(4-chloro-phenylazo)-4,5-difluoro-benzonitrile (3.3 g, 12 mmol) in ethanol (91 ml) under an argon atmosphere. The suspension was heated under reflux conditions for 16 h and the solvent removed under reduced pressure. The residue was taken up in half saturated aqueous NaHCO$_3$ solution/EtOAc 1/1, the layers were separated and filtered separately over dicalite. The filtrate of the aqueous layer was extracted two times with EtOAc, the organic layers were combined, washed with ice water and dried over Na$_2$SO$_4$. The solvent was removed under reduced pressure to give the title compound (3.2 g, 11 mmol; 95%) as light brown solid which was used in the next step without further purification. MS: m/e=280.0 [M+H$^+$].

16.4 [2-(4-Chloro-phenyl)-5,6-difluoro-2H-indazol-3-yl]-cyclohexyl-amine

In analogy to the procedure described in example 1.1, a mixture of 2-(4-chloro-phenyl)-5,6-difluoro-2H-indazol-3-ylamine and cyclohexanone ([108-94-1]) was reacted with sodium triacetoxyborohydride in the presence of acetic acid in CH$_2$Cl$_2$ under reflux conditions for 96 h to give the title compound as light brown solid. MS: m/e=362.5 [M+H$^+$].

16.5 3-Chloro-4-{3-[2-(4-chloro-phenyl)-5,6-difluoro-2H-indazol-3-yl]-3-cyclohexyl-ureido}-benzoic acid methyl ester In analogy to the procedure described in example 1.2, [2-(4-chloro-phenyl)-5,6-difluoro-2H-indazol-3-yl]-cyclohexyl-amine was reacted with 3-chloro-4-isocyanato-benzoic acid methyl ester (example 9.1) in 1,2-dichloroethane in the presence of Et$_3$N (1.4 eq.) for 4 d under reflux conditions to give the title compound as light brown gum. MS: m/e=573.0 [M+H$^+$].

16.6 3-Chloro-4-{3-[2-(4-chloro-phenyl)-5,6-difluoro-2H-indazol-3-yl]-3-cyclohexyl-ureido}-benzoic acid In analogy to the procedure described in example 2.2, 3-chloro-4-{3-[2-(4-chloro-phenyl)-5,6-difluoro-2H-indazol-3-yl]-3-cyclohexyl-ureido}-benzoic acid methyl ester was treated with 1 N aqueous lithium hydroxide solution in THF/MeOH 1/1 for 24 h at 60° C. to give the title compound as off-white solid. MS: m/e=559.3 [M+H$^+$].

Example 17

1-[2-(4-Chloro-phenyl)-2H-indazol-3-yl]-3-cyclohexyl-1-(2-methoxy-ethyl)-urea

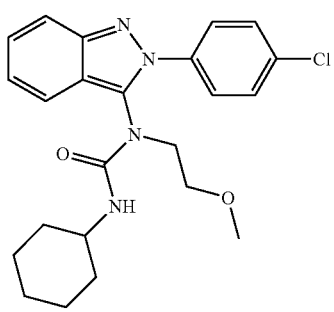

17.1 [2-(4-Chloro-phenyl)-2H-indazol-3-yl]-(2-methoxy-ethyl)-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with 2-methoxy-ethylamine ([109-85-3]) in N-methyl 2-pyrrolidone for 48 h at 175° C. in a sealed tube to give the title compound as yellow oil. MS: m/e=302.3 [M+H$^+$].

17.2 1-[2-(4-Chloro-phenyl)-2H-indazol-3-yl]-3-cyclohexyl-1-(2-methoxy-ethyl)-urea In analogy to the procedure described in example 1.2, [2-(4-chloro-phenyl)-2H-indazol-3-yl]-(2-methoxy-ethyl)-amine was reacted with cyclohexylisocyanate ([3173-53-3]) in toluene for 3 days under reflux conditions to give the title compound as brown foam. MS: m/e=427.4 [M+H$^+$].

Example 18

3-Chloro-4-{3-[2-(4-chloro-phenyl)-2H-indazol-3-yl]-3-phenyl-ureido}-benzoic acid methyl ester

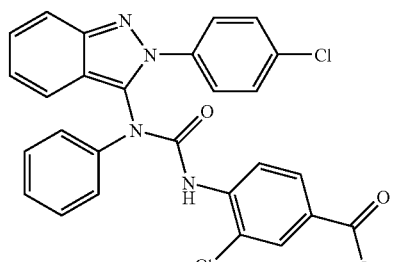

In analogy to the procedure described in example 1.2, [2-(4-chloro-phenyl)-2H-indazol-3-yl]-phenyl-amine (example 15.1) was reacted with 3-chloro-4-isocyanato-benzoic acid methyl ester (example 9.1) in toluene for 7 days under reflux conditions to give the title compound as yellow foam. MS: m/e=530.7 [M+H$^+$].

Example 19

1-(3-Chloro-phenyl)-1-[2-(4-chloro-phenyl)-2H-indazol-3-yl]-3-cyclohexyl-urea

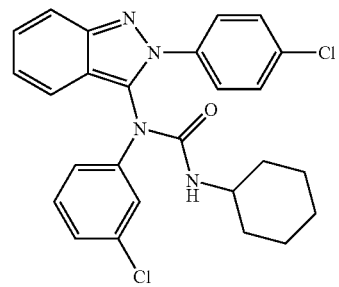

19.1 (3-Chloro-phenyl)-[2-(4-chloro-phenyl)-2H-indazol-3-yl]-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with 3-chloro-phenylamine ([108-42-9]) in N-methyl 2-pyrrolidone for 48 h at 175° C. in a sealed tube to give the title compound as off-white crystals. MS: m/e=354.2 [M+H$^+$].

19.2 1-(3-Chloro-phenyl)-1-[2-(4-chloro-phenyl)-2H-indazol-3-yl]-3-cyclohexyl-urea In analogy to the procedure described in example 1.2, (3-chloro-phenyl)-[2-(4-chloro-phenyl)-2H-indazol-3-yl]-amine was reacted with cyclohexylisocyanate ([3173-53-3]) in toluene for 3 d under reflux conditions to give the title compound as yellow foam. MS: m/e=479.3 [M+H$^+$].

Example 20

3-Chloro-4-[3-[2-(4-chloro-phenyl)-2H-indazol-3-yl]-3-(2-methoxy-ethyl)-ureido]-benzoic acid

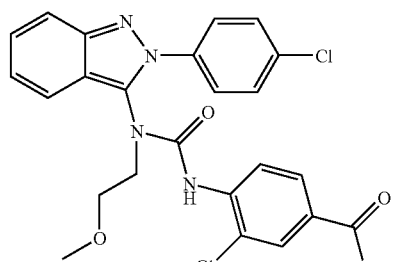

20.1 3-Chloro-4-[3-[2-(4-chloro-phenyl)-2H-indazol-3-yl]-3-(2-methoxy-ethyl)-ureido]-benzoic acid methyl ester In analogy to the procedure described in example 1.2, [2-(4-chloro-phenyl)-2H-indazol-3-yl]-(2-methoxy-ethyl)- amine (example 17.1) was reacted with 3-chloro-4-isocyanato-benzoic acid methyl ester (example 9.1) in toluene for 7 d under reflux conditions to give the title compound as yellow foam. MS: m/e=513.0 [M+H⁺].

20.2 3-Chloro-4-[3-[2-(4-chloro-phenyl)-2H-indazol-3-yl]-3-(2-methoxy-ethyl)-ureido]-benzoic acid In analogy to the procedure described in example 2.2, 3-chloro-4-[3-[2-(4-chloro-phenyl)-2H-indazol-3-yl]-3-(2-methoxy-ethyl)-ureido]-benzoic acid methyl ester was treated with 1 N aqueous lithium hydroxide solution in THF/MeOH 1/1 for 14 h at ambient temperature to give the title compound as yellow foam. MS: m/e=497.1 [M−H⁻].

Example 21

(3-Chloro-4-{3-[2-(4-chloro-phenyl)-2H-indazol-3-yl]-3-cyclohexyl-ureido}-phenyl)-acetic acid

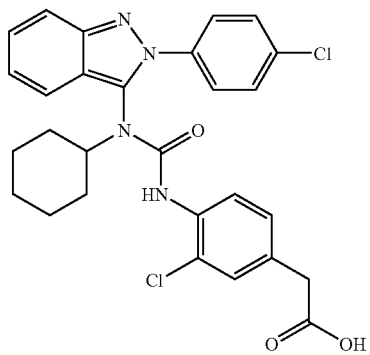

21.1 (4-Amino-3-chloro-phenyl)-acetic acid ethyl ester

N-Chlorosuccinimide (391 mg, 2.93 mmol) was added to a solution of (4-amino-phenyl)-acetic acid ethyl ester (500 mg, 2.79 mmol; [5438-70-0]) in acetonitrile (10 ml) under an argon atmosphere. The reaction mixture was heated to 50° C. for 1 h. The solvent was removed under reduced pressure and the residue taken up in iPrOAc/brine 1/1. The layers were separated and the aqueous layer was extracted with iPrOAc. The combined organic layers were dried over Na₂SO₄. The solvent was removed under reduced pressure and the residue was purified by column chromatography (silica gel, iPrOAc/heptane) to give the title compound (481 mg, 2.25 mmol; 81%) as brown oil. MS: m/e=214.1 [M+H⁺].

21.2 (3-Chloro-4-isocyanato-phenyl)-acetic acid ethyl ester

In analogy to the procedure described in example 9.1, (4-amino-3-chloro-phenyl)-acetic acid ethyl ester was reacted with triphosgene in the presence of Et₃N in CH₂Cl₂ under reflux conditions for 48 h to give the title compound as brown solid which was used in the next step without further purification. MS: m/e=257.0 [M+NH₄⁺].

21.3 (3-Chloro-4-{3-[2-(4-chloro-phenyl)-2H-indazol-3-yl]-3-cyclohexyl-ureido}-phenyl)-acetic acid ethyl ester In analogy to the procedure described in example 1.2, [2-(4-chloro-phenyl)-2H-indazol-3-yl]-cyclohexyl-amine (example 11.1) was reacted with (3-chloro-4-isocyanato-phenyl)-acetic acid ethyl ester in 1,2-dichloroethane in the presence of Et₃N (1.4 eq.) for 2 d under reflux conditions to give the title compound as brown gum. MS: m/e=565.3 [M+H⁺].

21.4 (3-Chloro-4-{3-[2-(4-chloro-phenyl)-2H-indazol-3-yl]-3-cyclohexyl-ureido}-phenyl)-acetic acid In analogy to the procedure described in example 2.2, (3-chloro-4-{3-[2-(4-chloro-phenyl)-2H-indazol-3-yl]-3-cyclohexyl-ureido}-phenyl)-acetic acid ethyl ester was treated with 1 N aqueous lithium hydroxide solution in THF/MeOH 1/1 for 14 h at ambient temperature to give the title compound as off-white solid. MS: m/e=536.8 [M+H⁺].

Example 22

4-{3-[2-(4-Chloro-phenyl)-2H-indazol-3-yl]-3-cyclohexyl-ureido}-3-methyl-benzoic acid

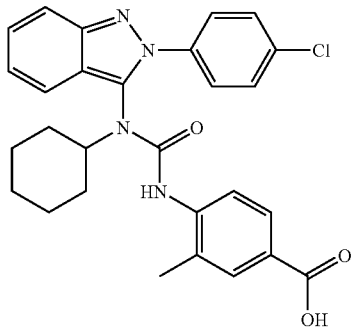

22.1 4-{3-[2-(4-Chloro-phenyl)-2H-indazol-3-yl]-3-cyclohexyl-ureido}-3-methyl-benzoic acid methyl ester In analogy to the procedure described in example 1.2, [2-(4-chloro-phenyl)-2H-indazol-3-yl]-cyclohexyl-amine (example 11.1) was reacted with 3-methyl-4-isocyanato-benzoic acid methyl ester (example 14.1) in 1,2-dichloroethane in the presence of Et₃N (1.4 eq.) for 2 days under reflux conditions to give the title compound as brown solid. MS: m/e=517.1 [M+H⁺].

22.2 4-{3-[2-(4-Chloro-phenyl)-2H-indazol-3-yl]-3-cyclohexyl-ureido}-3-methyl-benzoic acid In analogy to the procedure described in example 2.2, 4-{3-[2-(4-chloro-phenyl)-2H-indazol-3-yl]-3-cyclohexyl-ureido}-3-methyl-benzoic acid methyl ester was treated with 1 N aqueous lithium hydroxide solution in THF/MeOH 1/1 for 14 h at ambient temperature to give the title compound as yellow solid. MS: m/e=503.0 [M+H$^+$].

Example 23

3-Chloro-4-{3-[2-(4-chloro-phenyl)-2H-indazol-3-yl]-3-cyclohexyl-ureido}-benzoic acid

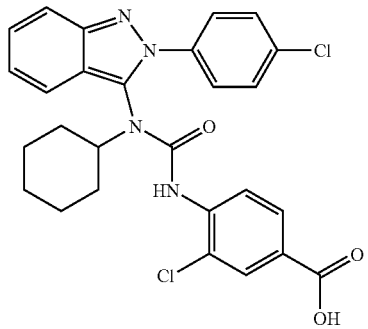

23.1 3-Chloro-4-{3-[2-(4-chloro-phenyl)-2H-indazol-3-yl]-3-cyclohexyl-ureido}-benzoic acid methyl ester In analogy to the procedure described in example 1.2, [2-(4-chloro-phenyl)-2H-indazol-3-yl]-cyclohexyl-amine (example 11.1) was reacted with 3-chloro-4-isocyanato-benzoic acid methyl ester (example 9.1) in 1,2-dichloroethane in the presence of Et$_3$N (1.4 eq.) for 2 days under reflux conditions to give the title compound as brown solid. MS: m/e=537.1 [M+H$^+$].

23.2 3-Chloro-4-{3-[2-(4-chloro-phenyl)-2H-indazol-3-yl]-3-cyclohexyl-ureido}-benzoic acid In analogy to the procedure described in example 2.2, 3-chloro-4-{3-[2-(4-chloro-phenyl)-2H-indazol-3-yl]-3-cyclohexyl-ureido}-benzoic acid methyl ester was treated with 1 N aqueous lithium hydroxide solution in THF/MeOH 1/1 for 14 h at ambient temperature to give the title compound as yellow solid. MS: m/e=521.0 [M−H$^−$].

Example 24

{4-[3-Cyclohexyl-3-(2-phenyl-2H-indazol-3-yl)-ureido]-3-fluoro-phenoxy}-acetic acid

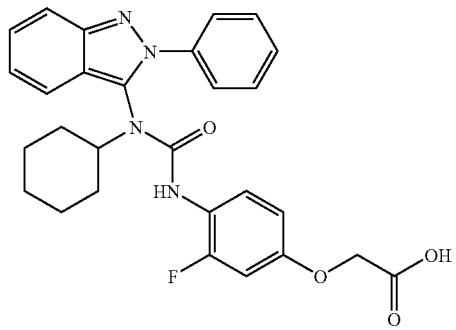

24.1 (3-Fluoro-4-isocyanato-phenoxy)-acetic acid methyl ester

In analogy to the procedure described in example 9.1, (4-amino-3-fluoro-phenoxy)-acetic acid methyl ester hydrochloride (Kori, Masakuni; Mild, Takashi; Nishimoto, Tomoyuki; Tozawa, Ryuichi. PCT Int. Appl. (2001), WO 2001098282 A1) was reacted with triphosgene in the presence of Et$_3$N (3.5 eq.) in CH$_2$Cl$_2$ under reflux conditions for 14 h to give the title compound as brown solid. MS: m/e=243.1 [M+NH$_4^+$].

24.2 {4-[3-Cyclohexyl-3-(2-phenyl-2H-indazol-3-yl)-ureido]-3-fluoro-phenoxy}-acetic acid methyl ester In analogy to the procedure described in example 1.2, cyclohexyl-(2-phenyl-2H-indazol-3-yl)-amine (example 1.1) was reacted with (3-fluoro-4-isocyanato-phenoxy)-acetic acid methyl ester in 1,2-dichloroethane in the presence of Et$_3$N (1.4 eq.) for 2 days under reflux conditions to give the title compound as yellow solid. MS: m/e=516.8 [M+H$^+$].

24.3 {4-[3-Cyclohexyl-3-(2-phenyl-2H-indazol-3-yl)-ureido]-3-fluoro-phenoxy}-acetic acid In analogy to the procedure described in example 2.2, {4-[3-cyclohexyl-3-(2-phenyl-2H-indazol-3-yl)-ureido]-3-fluoro-phenoxy}-acetic acid methyl ester was treated with 1 N aqueous lithium hydroxide solution in THF/MeOH 1/1 for 1 h at 60° C. to give the title compound as off-white solid. MS: m/e=501.0 [M−H$^−$].

Example 25

1-[2-(4-Chloro-phenyl)-2H-indazol-3-yl]-3-cyclohexyl-1-(3-ethoxy-phenyl)-urea

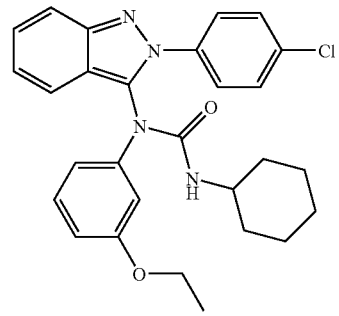

25.1 [2-(4-Chloro-phenyl)-2H-indazol-3-yl]-(3-ethoxy-phenyl)-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with 3-ethoxy-phenylamine ([621-33-0]) in N-methyl 2-pyrrolidone for 4 d at 175° C. in a sealed tube to give the title compound as yellow solid. MS: m/e=364.3 [M+H$^+$].

25.2 1-[2-(4-Chloro-phenyl)-2H-indazol-3-yl]-3-cyclohexyl-1-(3-ethoxy-phenyl)-urea In analogy to the procedure described in example 1.2, [2-(4-chloro-phenyl)-2H-indazol-3-yl]-(3-ethoxy-phenyl)-amine was reacted with cyclohexylisocyanate ([3173-53-3]) in 1,2-dichloroethane in the presence of Et$_3$N (3 eq.) for 3 d under reflux conditions to give the title compound as yellow solid. MS; m/e=489.1 [M+H$^+$].

Example 26

3-(4-{3-[2-(4-Chloro-phenyl)-2H-indazol-3-yl]-3-cyclohexyl-ureido}-3-fluoro-phenyl)-propionic acid

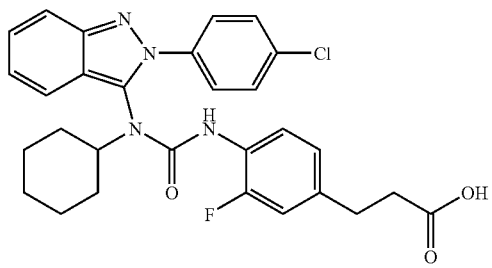

26.1 (E)-3-(3-Fluoro-4-nitro-phenyl)-acrylic acid tert-butyl ester

To a suspension of (tert-butoxycarbonylmethyl)triphenylphosphonium chloride (1.6 g, 3.9 mmol; [35000-37-4]) in tetrahydrofuran (10 ml) was added potassium tert-butoxide (0.44 g, 3.9 mmol). After stirring for 15 min 3-fluoro-4-nitrobenzaldehyde (0.60 g, 3.5 mmol; [160538-51-2]) was added. After 1.5 h the suspension was poured on water, the phases were separated and the aqueous phase extracted three times with ethyl acetate. The combined organic layers were washed with brine, dried over magnesium sulfate, filtered and evaporated. The residue was purified by flash-chromatography using a gradient of n-heptane:tert-butyl methyl ether (100:0 to 80:20) to give the title compound (804 mg, 3.01 mmol; 86%) as light brown solid. MS: m/e=194.0 [M–C$_4$H$_9$O$^+$].

26.2 3-(4-Amino-3-fluoro-phenyl)-propionic acid tert-butyl ester

A solution of (E)-3-(3-fluoro-4-nitro-phenyl)-acrylic acid tert-butyl ester (804 mg, 3.01 mmol) in ethyl acetate (10 ml) was hydrogenated on 10% palladium on charcoal for 30 min at 1.5 bar. The suspension was filtered, the filter cake washed with ethyl acetate and the filtrate evaporated and dried under high vacuum to give the product as light brown solid (713 mg, 3 mmol; 99%). This material was pure enough for the next step. MS: m/e=240.0 [M+H$^+$].

26.3 3-(3-Fluoro-4-isocyanato-phenyl)-propionic acid tert-butyl ester

In analogy to the procedure described in example 9.1, 3-(4-amino-3-fluoro-phenyl)-propionic acid tert-butyl ester was reacted with triphosgene in the presence of Et$_3$N in CH$_2$Cl$_2$ under reflux conditions for 20 h to give the title compound as yellow oil which was used in the next step without further purification. MS: m/e=265.1 [M$^+$].

26.4 3-(4-{3-[2-(4-Chloro-phenyl)-2H-indazol-3-yl]-3-cyclohexyl-ureido}-3-fluoro-phenyl)-propionic acid tert-butyl ester In analogy to the procedure described in example 1.2, [2-(4-chloro-phenyl)-2H-indazol-3-yl]-cyclohexyl-amine (example 9.1) was reacted with 3-(3-fluoro-4-isocyanato-phenyl)-propionic acid tert-butyl ester in 1,2-dichloroethane in the presence of Et$_3$N for 3 days under reflux conditions to give the title compound as brown oil. MS: m/e=591.3 [M+H$^+$].

26.5 3-(4-{3-[2-(4-Chloro-phenyl)-2H-indazol-3-yl]-3-cyclohexyl-ureido}-3-fluoro-phenyl)-propionic acid 3-(4-{3-[2-(4-Chloro-phenyl)-2H-indazol-3-yl]-3-cyclohexyl-ureido}-3-fluoro-phenyl)-propionic acid tert-butyl ester (20 mg, 34 µmol) was dissolved in a 4 M solution of HCl in dioxane (190 µl) under an argon atmosphere. The solution was stirred for 14 h at ambient temperature, poured onto ice water/1 N aqueous NaOH solution 1/1 and extracted two times with TBME. The aqueous layer was acidified with 1 N HCl and extracted two times with iPrOAc. The extracts were washed with ice water/brine 1/1 and dried over Na$_2$SO$_4$. The solvent was removed under reduced pressure and the residue was purified by preparative thin layer chromatography (silica gel, CH$_2$Cl$_2$/MeOH) to give the title compound (2 mg, 3.7 µmol; 12%) as yellow foam. MS: m/e=535.3 [M+H$^+$].

Example 27

3-{3-[2-(4-Chloro-phenyl)-2H-indazol-3-yl]-3-cyclohexyl-ureido}-2-methyl-benzoic acid

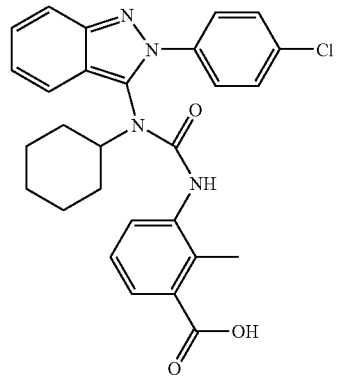

27.1 3-{3-[2-(4-Chloro-phenyl)-2H-indazol-3-yl]-3-cyclohexyl-ureido}-2-methyl-benzoic acid methyl ester In analogy to the procedure described in example 1.2, [2-(4-chloro-phenyl)-2H-indazol-3-yl]-cyclohexyl-amine (example 9.1) was reacted with 3-isocyanato-2-methyl-benzoic acid methyl ester ([480-439-28-9]) in 1,2-dichloroethane in the presence of Et₃N (1.4 eq.) for 3 days under reflux conditions to give the title compound as yellow oil. MS: m/e=517.2 [M+H⁺].

27.2 3-{3-[2-(4-Chloro-phenyl)-2H-indazol-3-yl]-3-cyclohexyl-ureido}-2-methyl-benzoic acid In analogy to the procedure described in example 2.2, 3-{3-[2-(4-chloro-phenyl)-2H-indazol-3-yl]-3-cyclohexyl-ureido}-2-methyl-benzoic acid methyl ester was treated with 1 N aqueous lithium hydroxide solution in THF/MeOH 1/1 for 14 h at ambient temperature to give the title compound as colorless solid. MS: m/e=503.4 [M+H⁺].

Example 28

1-(3-Chloro-4-fluoro-phenyl)-1-[2-(4-chloro-phenyl)-2H-indazol-3-yl]-3-cyclohexyl-urea

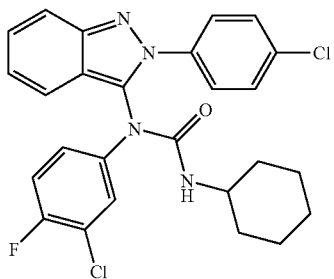

28.1 (3-Chloro-4-fluoro-phenyl)-[2-(4-chloro-phenyl)-2H-indazol-3-yl]-amine In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with 3-chloro-4-fluoro-phenylamine ([857091-30-6]) in N-methyl 2-pyrrolidone for 3 d at 175° C. in a sealed tube to give the title compound as grey crystals. MS: m/e=372.1 [M+H⁺].

28.2 1-(3-Chloro-4-fluoro-phenyl)-1-[2-(4-chloro-phenyl)-2H-indazol-3-yl]-3-cyclohexyl-urea In analogy to the procedure described in example 1.2, (3-chloro-4-fluoro-phenyl)-[2-(4-chloro-phenyl)-2H-indazol-3-yl]-amine was reacted with cyclohexylisocyanate ([3173-53-3]) in 1,2-dichloroethane in the presence of Et₃N (3 eq.) for 4 d under reflux conditions to give the title compound as yellow oil. MS: m/e=496.9 [M+H⁺].

Example 29

1-[5-Chloro-2-(4-chloro-phenyl)-2H-indazol-3-yl]-3-cyclohexyl-1-(3-ethoxy-phenyl)-urea

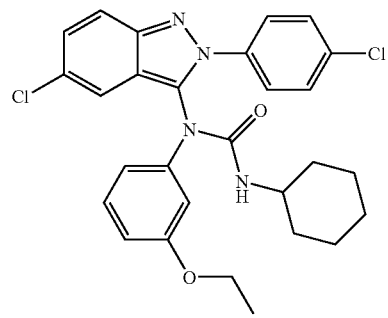

29.1 3,5-Dichloro-2-(4-chloro-phenyl)-2H-indazole and 3-chloro-2-(4-chloro-phenyl)-2H-indazole A solution of 2-azido-N-(4-chloro-phenyl)-benzamide (29.7 g, 109 mmol; Ardakani, Manouchehr; Smalley, Robert K.; Smith, Richard H. Synthesis (1979), (4), 308-9) in thionyl chloride (213 ml) was heated under reflux conditions for 8 h under an argon atmosphere. Thionyl chloride was removed under reduced pressure. The residue was taken up in ice water/saturated aqueous NaHCO₃ solution 1/1 and extracted two times with CH₂Cl₂. The combined extracts were washed with ice water/saturated aqueous NaHCO₃ solution 1/1, ice water/brine 1/1 and dried over Na₂SO₄. The solvent was removed under reduced pressure and the residue was purified by crystallization (CH₂Cl₂/heptane) to give a mixture (20.4 g) of 3,5-dichloro-2-(4-chloro-phenyl)-2H-indazole (side product) and 3-chloro-2-(4-chloro-phenyl)-2H-indazole (main product) which was used in the next step without further purification. 3,5-Dichloro-2-(4-chloro-phenyl)-2H-indazole: MS: m/e=296.0 [M⁺]. 3-Chloro-2-(4-chloro-phenyl)-2H-indazole: MS: m/e=262.0 [M⁺].

29.2 [5-Chloro-2-(4-chloro-phenyl)-2H-indazol-3-yl]-(3-ethoxy-phenyl)-amine In analogy to the procedure described in example 4.1, a mixture of 3,5-dichloro-2-(4-chloro-phenyl)-2H-indazole and 3-chloro-2-(4-chloro-phenyl)-2H-indazole was reacted with 3-ethoxy-phenylamine ([621-33-0]) in N-methyl 2-pyrrolidone for 4 d at 175° C. in a sealed tube to give the title compound after purification by column chromatography (silica gel, iPrOAc/heptane) as yellow foam. MS: m/e=398.1 [M+H⁺].

29.3 1-[5-Chloro-2-(4-chloro-phenyl)-2H-indazol-3-yl]-3-cyclohexyl-1-(3-ethoxy-phenyl)-urea In analogy to the procedure described in example 1.2, [5-chloro-2-(4-chloro-phenyl)-2H-indazol-3-yl]-(3-ethoxy-phenyl)-amine was reacted with cyclohexylisocyanate ([3173-53-3]) in 1,2-dichloroethane in the presence of Et₃N Example 30

(4-{3-[2-(4-Chloro-phenyl)-2H-indazol-3-yl]-3-cyclohexyl-ureido}-3-fluoro-phenoxy)-acetic acid methyl ester

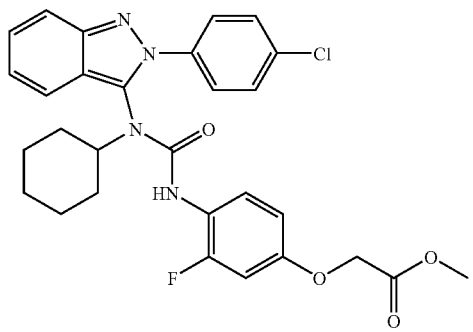

In analogy to the procedure described in example 1.2, [2-(4-chloro-phenyl)-2H-indazol-3-yl]-cyclohexyl-amine (example 9.1) was reacted with (3-fluoro-4-isocyanato-phenoxy)-acetic acid methyl ester (example 24.1) in 1,2-dichloroethane in the presence of Et$_3$N (2.2 eq.) for 3 days under reflux conditions to give the title compound as brown gum. MS: m/e=551.3 [M+H$^+$].

Example 31

3-Chloro-4-{3-[2-(4-chloro-phenyl)-2H-indazol-3-yl]-3-cyclobutyl-ureido}-benzoic acid

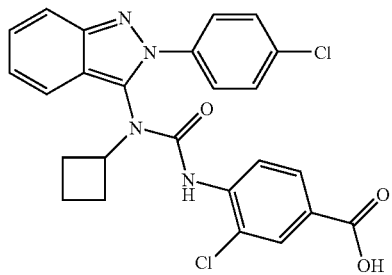

31.1 [2-(4-Chloro-phenyl)-2H-indazol-3-yl]-cyclobutyl-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with cyclobutylamine ([2516-34-9]) in N-methyl 2-pyrrolidone for 3 days at 175° C. in a sealed tube to give the title compound as yellow solid. MS: m/e=298.4 [M+H$^+$].

31.2 3-Chloro-4-{3-[2-(4-chloro-phenyl)-2H-indazol-3-yl]-3-cyclobutyl-ureido}-benzoic acid methyl ester In analogy to the procedure described in example 1.2, [2-(4-chloro-phenyl)-2H-indazol-3-yl]-cyclobutyl-amine was reacted with 3-chloro-4-isocyanato-benzoic acid methyl ester (example 9.1) in 1,2-dichloroethane in the presence of Et$_3$N (3 eq.) for 3 days under reflux conditions to give the title compound as yellow oil. MS: m/e=509.4 [M+H$^+$].

31.3 3-Chloro-4-{3-[2-(4-chloro-phenyl)-2H-indazol-3-yl]-3-cyclobutyl-ureido}-benzoic acid In analogy to the procedure described in example 2.2, 3-chloro-4-{3-[2-(4-chloro-phenyl)-2H-1-indazol-3-yl]-3-cyclobutyl-ureido}-benzoic acid methyl ester was treated with 1 N aqueous lithium hydroxide solution in THF/MeOH 1/1 for 14 h at ambient temperature to give the title compound as yellow foam. MS: m/e=495.3 [M+H$^+$].

Example 32

2-(4-{3-[2-(4-Chloro-phenyl)-2H-indazol-3-yl]-3-cyclohexyl-ureido}-3-fluoro-phenyl)-2-methyl-propionic acid

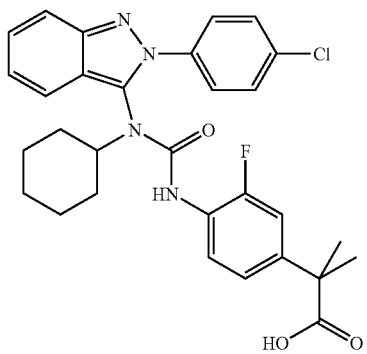

32.1 2-(3-Fluoro-4-isocyanato-phenyl)-2-methyl-propionic acid methyl ester

In analogy to the procedure described in example 9.1, 2-(4-amino-3-fluoro-phenyl)-2-methyl-propionic acid methyl ester (Chung, Jae-Uk; Kim, Su Yeon; Lim, Ju-Ok; Choi, Hyun-Kyung; Kang, Sang-Uk; Yoon, Hae-Seok; Ryu, HyungChul; Kang, Dong Wook; Lee, Jeewoo; Kang, Bomi; Choi, Sun; Toth, Attila; Pearce, Larry V.; Pavlyukovets, Vladimir A.; Lundberg, Daniel J.; Blumberg, Peter M. Bioorganic & Medicinal Chemistry (2007), 15(18), 6043-6053) was reacted with triphosgene in the presence of Et$_3$N in CH$_2$Cl$_2$ under reflux conditions for 16 h to give the title compound as brown oil which was used in the next step without further purification. MS: m/e=255.4 [M+NH$_4^+$].

32.2 2-(4-{3-[2-(4-Chloro-phenyl)-2H-indazol-3-yl]-3-cyclohexyl-ureido}-3-fluoro-phenyl)-2-methyl-propionic acid methyl ester In analogy to the procedure described in example 1.2, [2-(4-chloro-phenyl)-2H-indazol-3-yl]-cyclohexyl-amine (example 9.1) was reacted with 2-(3-fluoro-4-isocyanato-phenyl)-2-methyl-propionic acid methyl ester in 1,2-dichloroethane in the presence of Et$_3$N for 3 days under reflux conditions to give the title compound as yellow solid. MS: m/e=563.5 [M+H$^+$].

32.3 2-(4-{3-[2-(4-Chloro-phenyl)-2H-indazol-3-yl]-3-cyclohexyl-ureido}-3-fluoro-phenyl)-2-methyl-propionic acid In analogy to the procedure described in example 2.2, 2-(4-{3-[2-(4-chloro-phenyl)-2H-indazol-3-yl]-3-cyclohexyl-ureido}-3-fluoro-phenyl)-2-methyl-propionic acid methyl ester was treated with 1 N aqueous lithium hydroxide solution in THF/MeOH 1/1 for 14 h at ambient temperature to give the title compound as yellow solid. MS: m/e=549.3 [M+H$^+$].

Example 33

3-{3-[2-(4-Chloro-phenyl)-2H-indazol-3-yl]-3-cyclohexyl-ureido}-4-methyl-benzoic acid

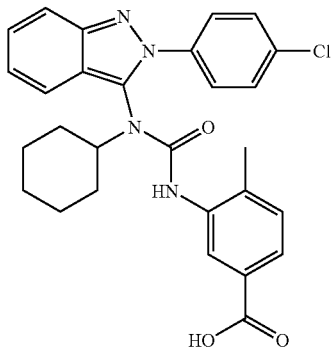

33.1 3-Isocyanato-4-methyl-benzoic acid methyl ester

In analogy to the procedure described in example 9.1, 3-amino-4-methyl-benzoic acid methyl ester ([18595-18-1]) was reacted with triphosgene in the presence of Et$_3$N in CH$_2$Cl$_2$ under reflux conditions for 16 h to give the title compound as brown solid which was used in the next step without further purification. MS: m/e=191 [M$^+$].

33.2 3-{3-[2-(4-Chloro-phenyl)-2H-indazol-3-yl]-3-cyclohexyl-ureido}-4-methyl-benzoic acid methyl ester In analogy to the procedure described in example 1.2, [2-(4-chloro-phenyl)-2H-indazol-3-yl]-cyclohexyl-amine (example 9.1) was reacted with 3-isocyanato-4-methyl-benzoic acid methyl ester in 1,2-dichloroethane in the presence of Et$_3$N (2.2 eq.) for 3 days under reflux conditions to give the title compound as yellow oil. MS: m/e=517.2 [M+H$^+$].

33.3 3-{3-[2-(4-Chloro-phenyl)-2H-indazol-3-yl]-3-cyclohexyl-ureido}-4-methyl-benzoic acid In analogy to the procedure described in example 2.2, 3-{3-[2-(4-chloro-phenyl)-2H-indazol-3-yl]-3-cyclohexyl-ureido}-4-methyl-benzoic acid methyl ester was treated with 1 N aqueous lithium hydroxide solution in THF/MeOH 1/1 for 14 h at ambient temperature to give the title compound as yellow solid. MS: m/e=503.3 [M+H$^+$].

Example 34

N-[2-(4-Chloro-phenyl)-2H-indazol-3-yl]-C-dicyclohexyl-methanesulfonamide

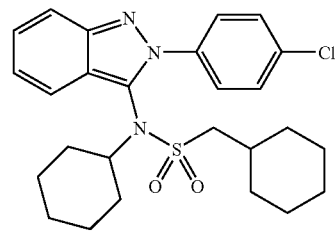

To an ice cold suspension of NaH (6 mg, 161 µmol) in DMF (3 ml) under an argon atmosphere was added a solution of [2-(4-chloro-phenyl)-2H-indazol-3-yl]-cyclohexyl-amine (50 mg, 153 µmol; example 11.1) in DMF (1 ml) within 10 min. The suspension was stirred for 1 h at 0° C. A solution of cyclohexyl-methanesulfonyl chloride (33 mg, 168 µmol; [4352-30-1]) in DMF (1 ml) was added within 5 min. The reaction mixture was stirred for 14 h at ambient temperature, poured onto ice water/brine 1/1 and extracted two times with iPrOAc. The combined extracts were washed with ice water/brine 1/1 and dried over Na$_2$SO$_4$. The solvent was removed under reduced pressure and the residue was purified by column chromatography (silica gel, iPrOAc/heptane) to give the title compound (21 mg, 43 µmol; 28%) as colorless foam. MS: m/e=486.1 [M+H$^+$].

Example 35

1-(3-Chloro-phenyl)-1-[2-(3-chloro-phenyl)-6-fluoro-2H-indazol-3-yl]-3-cyclohexyl-urea

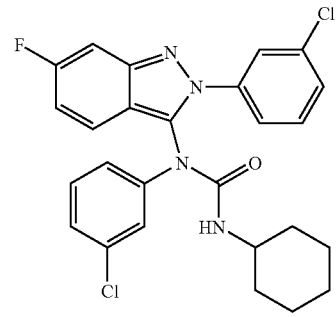

35.1 (3-Chloro-phenyl)-[2-(3-chloro-phenyl)-6-fluoro-2H-indazol-3-yl]-amine 3-Chloroaniline (12.4 ml, 118 mmol; [108-42-9]) and Na$_2$SO$_4$ (3.36 g, 24 mmol) were added to a solution of 4-fluoro-2-nitro-benzaldehyde (1 g, 6 mmol; [2923-96-8]) in THF (12 ml) under an argon atmosphere. The suspension was stirred at 50° C. for 16 h. Na$_2$SO$_4$ was removed, indium (2.04 g, 18 mmol) and iodine (1.2 g, 5 mmol) were added and the reaction mixture was stirred at 50° C. for 24 h. The mixture was filtered over celite and the filtrate was poured onto 1 M aqueous HCl solution/iPrOAc 1/1. The aqueous layer was extracted one more time with iPrOAc and the combined extracts were washed with brine and dried over Na$_2$SO$_4$. The solvent was removed under reduced pressure and the residue was purified by crystallization (CH$_2$Cl$_2$) to give the title compound (672 mg, 1.8 mmol; 31%) as white powder. MS: m/e=372.0 [M+H$^+$].

35.2 1-(3-Chloro-phenyl)-1-[2-(3-chloro-phenyl)-6-fluoro-2H-indazol-3-yl]-3-cyclohexyl-urea In analogy to the procedure described in example 1.2, (3-chloro-phenyl)-[2-(3-chloro-phenyl)-6-fluoro-2H-indazol-3-yl]-amine was reacted with cyclohexylisocyanate ([3173-53-3]) in 1,2-dichloroethane in the presence of Et$_3$N (3 eq.) for 3 d under reflux conditions to give the title compound as white solid. MS: m/e=497.3 [M+H$^+$].

Example 36

N-[2-(4-Chloro-phenyl)-2H-indazol-3-yl]-2,N-dicyclohexyl-acetamide

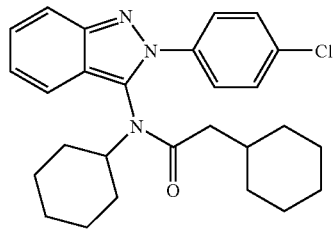

To an ice cold suspension of NaH (13 mg, 340 µmol) in DMF (5 ml) under an argon atmosphere was added a solution of [2-(4-chloro-phenyl)-2H-indazol-3-yl]-cyclohexyl-amine (100 mg, 310 µmol; example 11.1) in DMF (1 ml) within 10 min. The suspension was stirred for 1 h at 0° C. A solution of cyclohexyl-acetyl chloride (50 µl, 340 µmol; [23860-35-7]) in DMF (1 ml) was added within 5 min. The reaction mixture was stirred for 14 h at ambient temperature, poured onto ice water/brine 1/1 and extracted two times with iPrOAc. The combined extracts were washed with ice water/brine 1/1 and dried over Na$_2$SO$_4$. The solvent was removed under reduced pressure and the residue was purified by column chromatography (silica gel, iPrOAc/heptane) to give the title compound (8 mg, 20 µmol; 6%) as yellow oil. MS: m/e=450.0 [M+H$^+$].

Example 37

[2-(4-Chloro-phenyl)-2H-indazol-3-yl]-cyclohexyl-carbamic acid cyclohexyl ester

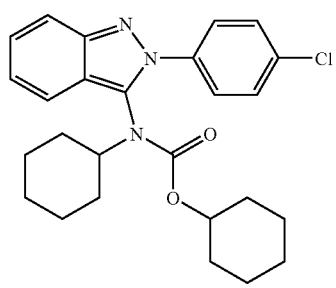

To an ice cold suspension of NaH (6 mg, 160 umol) in DMF (3 ml) under an argon atmosphere was added a solution of [2-(4-chloro-phenyl)-2H-indazol-3-yl]-cyclohexyl-amine (50 mg, 153 µmol; example 11.1) in DMF (1 ml) within 10 min. The suspension was stirred for 1 h at ambient temperature. A solution of cyclohexyl chloroformate (33 mg, 203 µmol; [13248-54-9]) in DMF (1 ml) was added within 5 min. The reaction mixture was stirred for 14 h at ambient temperature, poured onto ice water/brine 1/1 and extracted two times with iPrOAc. The combined extracts were washed with brine and dried over Na$_2$SO$_4$. The solvent was removed under reduced pressure and the residue was purified by preparative thin layer chromatography (silica gel, iPrOAc/heptane) to give the title compound (3 mg, 7 µmol; 3%) as brown solid. MS: m/e=452.4 [M+H$^+$].

Example 38

1-[2-(4-Chloro-phenyl)-2H-indazol-3-yl]-1,3-dicyclopentyl-urea

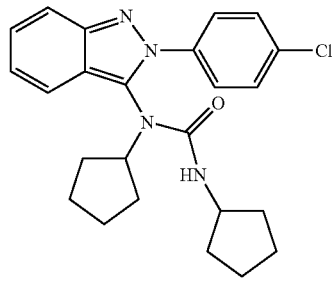

To an ice cold suspension of NaH (6 mg, 160 umol) in DMF (2.5 ml) under an argon atmosphere was added a solution of [2-(4-chloro-phenyl)-2H-indazol-3-yl]-cyclohexyl-amine (50 mg, 153 umol; example 11.1) in DMF (1 ml) within 10 min. The suspension was stirred for 1 h at 0° C. A solution of isocyanato-cyclopentane (34 mg, 306 umol; [4747-71-1]) in DMF (0.5 ml) was added within 5 min. The reaction mixture was stirred for 1 h at ambient temperature, poured onto ice water/1 N aqueous HCl solution/brine 1/1/1 and extracted two times with iPrOAc. The combined extracts were washed with brine and dried over Na$_2$SO$_4$. The solvent was removed under reduced pressure and the residue was purified by preparative thin layer chromatography (silica gel, iPrOAc/heptane) to give the title compound (20 mg, 47 umol; 21%) as yellow foam. MS: m/e=423.1 [M+H$^+$].

Example 39

N-[2-(4-Chloro-phenyl)-2H-indazol-3-yl]-N-cyclohexyl-2-phenyl-acetamide

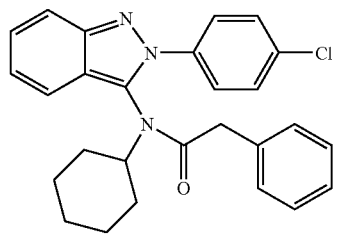

To an ice cold suspension of NaH (13 mg, 320 umol) in DMF (3 ml) under an argon atmosphere was added a solution of [2-(4-chloro-phenyl)-2H-indazol-3-yl]-cyclohexyl-amine (100 mg, 310 μmol; example 11.1) in DMF (1 ml) within 10 min. The suspension was stirred for 1 h at 0° C. A solution of phenyl-acetyl chloride (40 μl, 340 μmol; [103-80-0]) in DMF (1 ml) was added within 5 min. The reaction mixture was stirred for 14 h at ambient temperature, poured onto ice water/brine 1/1 and extracted two times with iPrOAc. The combined extracts were washed with ice water/brine 1/1 and dried over Na$_2$SO$_4$. The solvent was removed under reduced pressure and the residue was purified by preparative thin layer chromatography (silica gel, iPrOAc/heptane) to give the title compound (10 mg, 23 μmol; 7%) as off-white solid. MS: m/e=444.1 [M+H$^+$].

Example 40

1-[2-(4-Chloro-phenyl)-6-fluoro-2H-indazol-3-yl]-1,3-dicyclohexyl-urea

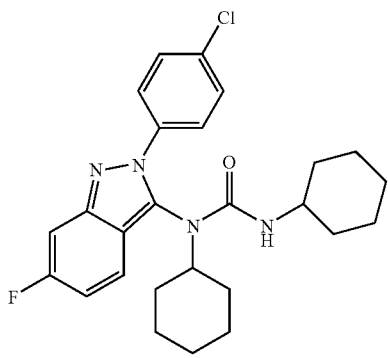

40.1
2-Azido-N-(4-chloro-phenyl)-4-fluoro-benzamide

2-Azido-4-fluoro-benzoic acid (3.01 g, 17 mmol; Barral, Karine; Moorhouse, Adam D.; Moses, John E. Organic Letters (2007), 9(9), 1809-1811) was dissolved at ambient temperature in thionyl chloride (27.3 ml) under an argon atmosphere. The reaction mixture was heated to 80° C. for 1.5 h and brought to dryness under reduced pressure to give 2-azido-4-fluoro-benzoyl chloride as orange oil. 2-Azido-4-fluoro-benzoyl chloride was dissolved at ambient temperature in CH$_2$Cl$_2$ (23 ml) under an argon atmosphere. 4-Chlorophenylamine (2.12 g, 17 mmol; [106-47-8]) was added and the reaction mixture was stirred at ambient temperature for 14 h. Saturated aqueous NaHCO$_3$ solution was added until a pH of 8 was adjusted, the layers were separated and the aqueous layer was extracted two more times with CH$_2$Cl$_2$. The combined extracts were washed with ice water/brine 1/1 and dried over Na$_2$SO$_4$. The solvent was removed under reduced pressure to give a brown solid which was crystallized from heptane/CH$_2$Cl$_2$ to give the title compound (3.08 g, 11 mmol; 64%) as off-white crystals. MS: m/e=291.0 [M+H$^+$].

40.2 3-Chloro-2-(4-chloro-phenyl)-6-fluoro-2H-indazole

2-Azido-N-(4-chloro-phenyl)-4-fluoro-benzamide (2.7 g, 1 mmol) was dissolved at ambient temperature in thionyl chloride (18.2 ml) under an argon atmosphere. The reaction mixture was heated under reflux conditions for 14 h and brought to dryness under reduced pressure. The residue was taken up in ice water/saturated aqueous NaHCO$_3$ solution 1/1 and CH$_2$Cl$_2$. The layers were separated and the aqueous layer was extracted one more time with CH$_2$Cl$_2$. The combined extracts were washed with ice water/brine 1/1 and dried over Na$_2$SO$_4$. The solvent was removed under reduced pressure to give the title compound (2.47 g, 8.8 mmol; 95%) as yellow solid. MS: m/e=280.9 [M+H$^+$].

40.3 [2-(4-Chloro-phenyl)-6-fluoro-2H-indazol-3-yl]-cyclohexyl-amine

In analogy to the procedure described in example 4.1, 3-chloro-2-(4-chloro-phenyl)-6-fluoro-2H-indazole was reacted with cyclohexylamine ([108-91-8]) in N-methyl 2-pyrrolidone for 72 h at 150° C. in a sealed tube to give the title compound as yellow solid. MS: m/e=344.5 [M+H$^+$].

40.4 1-[2-(4-Chloro-phenyl)-6-fluoro-2H-indazol-3-yl]-1,3-dicyclohexyl-urea

In analogy to the procedure described in example 1.2, [2-(4-chloro-phenyl)-6-fluoro-2H-indazol-3-yl]-cyclohexyl-amine was reacted with cyclohexylisocyanate ([3173-53-3]) in toluene for 5 days under reflux conditions to give the title compound as off-white solid. MS: m/e=469.4 [M+H$^+$].

Example 41 trans-1-(3-Chloro-phenyl)-1-[2-(4-chloro-phenyl)-2H-indazol-3-yl]-3-(4-hydroxy-cyclohexyl)-urea

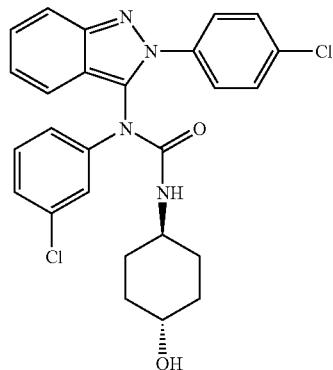

41.1 trans-3-[4-(tert-Butyl-dimethyl-silanyloxy)-cyclohexyl]-1-(3-chloro-phenyl)-1-[2-(4-chloro-phenyl)-2H-indazol-3-yl]-urea In analogy to the procedure described in example 1.2, (3-chloro-phenyl)-[2-(4-chloro-phenyl)-2H-indazol-3-yl]-amine (example 19.1) was reacted with trans-tert-butyl-(4-isocyanato-cyclohexyloxy)-dimethyl-silane (Dermatakis, Apostolos; Kabat, Marek Michal; Luk, Kin-Chun; Rossman, Pamela Loreen; So, Sung-Sau. PCT Int. Appl. (2004), WO 2004041822 A1) in 1,2-dichloroethane in the presence of Et$_3$N (3 eq.) for 6 days under reflux conditions to give the title compound as brown solid. MS: m/e=611.2 [M+H$^+$].

41.2 trans-1-(3-Chloro-phenyl)-1-[2-(4-chloro-phenyl)-2H-indazol-3-yl]-3-(4-hydroxy-cyclohexyl)-urea Hydrofluoric acid (48%, 200 μl, 16 μmol) was added to a solution of trans-3-[4-(tert-butyl-dimethyl-silanyloxy)-cyclohexyl]-1-(3-chloro-phenyl)-1-[2-(4-chloro-phenyl)-2H-indazol-3-yl]-urea (10 mg, 16 μmol) in CH₃CN/CH₂Cl₂ 1/1 (400 μl). The reaction mixture was stirred for 4 h at ambient temperature, diluted with CH₂Cl₂ (5 ml) and washed with saturated aqueous NaHCO₃ solution and brine. The organic layer was dried over Na₂SO₄. The solvent was removed under reduced pressure to give the title compound (2 mg, 4 μmol; 25%) as brown solid. MS: m/e=495.5 [M+H⁺].

Example 42

1-[2-(4-Chloro-phenyl)-2H-indazol-3-yl]-3-cyclohexyl-1-pyridin-3-yl-urea

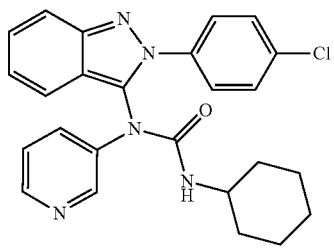

42.1 [2-(4-Chloro-phenyl)-2H-indazol-3-yl]-pyridin-3-yl-amine

In analogy to the procedure described in example 4.1, 3-chloro-2-(4-chloro-phenyl)-2H-indazole (Ardakani, Manouchehr; Smalley, Robert K.; Smith, Richard H., Synthesis (1979), (4), 308-9) was reacted with 3-iminopyridine ([462-08-8]) in N-methyl 2-pyrrolidone for 4 days at 175° C. in a sealed tube to give the title compound as yellow solid. MS: m/e=321.1 [M+H⁺].

42.2 1-[2-(4-Chloro-phenyl)-2H-indazol-3-yl]-3-cyclohexyl-1-pyridin-3-yl-urea In analogy to the procedure described in example 1.2, [2-(4-chloro-phenyl)-2H-indazol-3-yl]-pyridin-3-yl-amine was reacted with cyclohexylisocyanate ([3173-53-3]) in 1,2-dichloroethane in the presence of Et₃N (3 eq.) for 3 days under reflux conditions to give the title compound as colorless oil. MS: m/e=446.0 [M+H⁺].

Example 43

1-(3-Chloro-phenyl)-1-[2-(3-chloro-phenyl)-5,6-difluoro-2H-indazol-3-yl]-3-cyclohexyl-urea

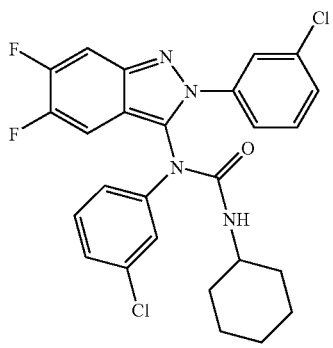

43.1 (3-Chloro-phenyl)-[2-(3-chloro-phenyl)-5,6-difluoro-2H-indazol-3-yl]-amine In analogy to the procedure described in example 35.1, 3-chloroaniline was reacted with 4,5-difluoro-2-nitro-benzaldehyde (Daubie, Christophe; Legrand, Jean Jacques; Pemberton, Clive. Eur. Pat. Appl. (1993), EP 538 100 A1) in the presence of Na₂SO₄, indium and iodine to give the title compound as brown solid. MS: m/e=388.0 [M−H⁻].

43.2 1-(3-Chloro-phenyl)-1-[2-(3-chloro-phenyl)-5,6-difluoro-2H-indazol-3-yl]-3-cyclohexyl-urea In analogy to the procedure described in example 1.2, (3-chloro-phenyl)-[2-(3-chloro-phenyl)-5,6-difluoro-2H-indazol-3-yl]-amine was reacted with cyclohexylisocyanate ([3173-53-3]) in 1,2-dichloroethane in the presence of Et₃N (3 eq.) for 3 d under reflux conditions to give the title compound as white solid. MS: m/e=515.4 [M+H⁺].

Example 44

1-(3-Chloro-phenyl)-1-[2-(4-chloro-phenyl)-6-fluoro-2H-indazol-3-yl]-3-cyclohexyl-urea

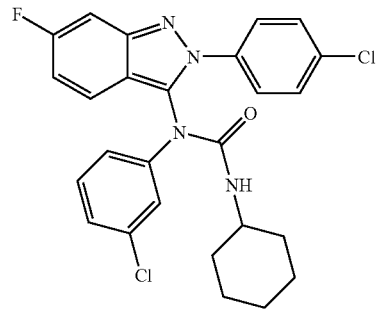

44.1 (3-Chloro-phenyl)-[2-(4-chloro-phenyl)-6-fluoro-2H-indazol-3-yl]-amine In analogy to the procedure described in example 4.1, 3-chloro-2-(4-chloro-phenyl)-6-fluoro-2H-indazole (example 40.2) was reacted with 3-chloro-phenylamine ([108-42-9]) in N-methyl 2-pyrrolidone for 72 h at 175° C. in a sealed tube to give the title compound as colorless crystals. MS: m/e=372.1 [M+H⁺].

44.2 1-(3-Chloro-phenyl)-1-[2-(4-chloro-phenyl)-6-fluoro-2H-indazol-3-yl]-3-cyclohexyl-urea In analogy to the procedure described in example 1.2, (3-chloro-phenyl)-[2-(4-chloro-phenyl)-6-fluoro-2H-indazol-3-yl]-amine was reacted with cyclohexylisocyanate ([3173-53-3]) in 1,2-dichloroethane in the presence of Et₃N (3 eq.) for 4 days under reflux conditions to give the title compound as yellow foam. MS: m/e=497.1 [M+H⁺].

Example 45

Cyclohexyl-(2-phenyl-4,5,6,7-tetrahydro-2H-indazol-3-yl)-amine

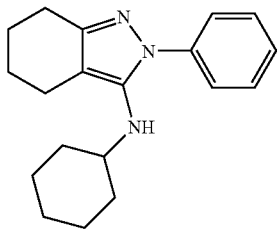

In analogy to the procedure described in example 1.1, a mixture of 2-phenyl-4,5,6,7-tetrahydro-2H-indazol-3-ylamine (Andrew, Herbert F.; Buckley, Donald. (1963), GB 926327) and cyclohexanone ([108-94-1]) was reacted with sodium triacetoxyborohydride in the presence of acetic acid in CH$_2$Cl$_2$ under reflux conditions for 5 h to give the title compound as colorless oil. MS: m/e=296.4 [M+H$^+$].

Example 46

1,3-Dicyclohexyl-1-(2-phenyl-4,5,6,7-tetrahydro-2H-indazol-3-yl)-urea

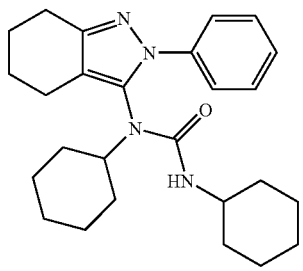

In analogy to the procedure described in example 1.2, cyclohexyl-(2-phenyl-4,5,6,7-tetrahydro-2H-indazol-3-yl)-amine (example 45) was reacted with cyclohexylisocyanate ([3173-53-3]) to give the title compound as colorless oil. MS: m/e=421.3 [M+H$^+$].

Example 47

3-Chloro-4-[3-cyclohexyl-3-(2-phenyl-4,5,6,7-tetrahydro-2H-indazol-3-yl)-ureido]-benzoic acid

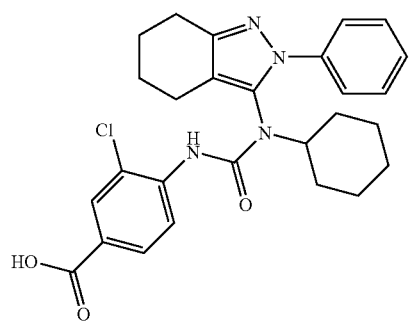

47.1 3-Chloro-4-[3-cyclohexyl-3-(2-phenyl-4,5,6,7-tetrahydro-2H-indazol-3-yl)-ureido]-benzoic acid methyl ester In analogy to the procedure described in example 1.2, cyclohexyl-(2-phenyl-4,5,6,7-tetrahydro-2H-indazol-3-yl)-amine (example 45) was reacted with 3-chloro-4-isocyanato-benzoic acid methyl ester (example 9.1) in 1,2-dichloroethane in the presence of triethylamine for 120 h under reflux conditions to give the title compound as yellow solid. MS: m/e=507.2 [M+H$^+$].

47.2 3-Chloro-4-[3-cyclohexyl-3-(2-phenyl-4,5,6,7-tetrahydro-2H-indazol-3-yl)-ureido]-benzoic acid In analogy to the procedure described in example 2.2, 3-chloro-4-[3-cyclohexyl-3-(2-phenyl-4,5,6,7-tetrahydro-2H-indazol-3-yl)-ureido]-benzoic acid methyl ester was treated with 1 N aqueous lithium hydroxide solution in THF/MeOH 1/1 for 1 h at ambient temperature to give the title compound as yellow solid. MS: m/e=493.3 [M+H$^+$].

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula I | 3.0 mg |
|---|---|
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula I | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound of the formula:

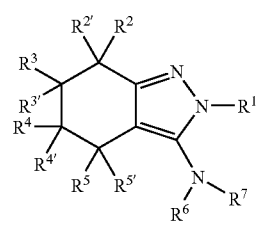

or a pharmaceutically acceptable salt thereof, wherein:
$R^1$ is a ring selected from the group consisting of phenyl, naphthyl and heteroaryl, said ring being unsubstituted or substituted with 1 to 3 substituents independently selected from the group consisting of: (1) lower alkyl, (2) halogen, (3) lower halogenalkyl, (4) hydroxy, (5) lower alkoxy, (6) lower halogenalkoxy and (7) cyano;
$R^2$, $R^3$, $R^4$ and $R^5$ independently from each other are selected from the group consisting of hydrogen, halogen and lower alkyl;
$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;
$R^6$ is selected from the group consisting of:
  (1) cycloalkyl,
  (2) lower alkoxyalkyl,
  (3) unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, lower alkoxycarbonyl, lower alkoxycarbonylalkyl, lower carboxylalkoxy, lower alkoxycarbonylalkoxy and cyano,
  (4) lower phenylalkyl, wherein the phenyl group is unsubstituted or substituted with 1 to 3 substituents independently selected from the group consisting of lower alkyl, halogen, lower halogenalkyl, hydroxy, lower alkoxy, lower halogenalkoxy and cyano,
  (5) heterocyclyl, and
  (6) unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano;
$R^7$ is selected from the group consisting of, (1) —C(O)—NH—$R^8$, (2) —C(O)—$R^9$, (3) —S(O)$_2$—$R^{10}$, and (4) —C(O)—O$R^{11}$;
$R^8$ is selected from the group consisting of:
  (1) lower alkyl,
  (2) cycloalkyl,
  (3) lower cycloalkylalkyl,
  (4) cycloalkyl substituted by hydroxy, carboxyl, tetrazolyl or lower carboxylalkyl,
  (5) heterocyclyl, and
  (6) unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;

$R^9$ is selected from the group consisting of:
(1) lower alkyl,
(2) cycloalkyl,
(3) lower cycloalkylalkyl, and
(4) lower phenylalkyl, wherein the phenyl group of said lower phenylalkyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;

$R^{10}$ is selected from the group consisting of:
(1) lower alkyl,
(2) cycloalkyl,
(3) lower cycloalkylalkyl, and
(4) lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl; and $R^{11}$ is selected from the group consisting of:
(1) lower alkyl,
(2) cycloalkyl,
(3) lower cycloalkylalkyl,
(4) cycloalkyl substituted by hydroxy, carboxyl, tetrazolyl or lower carboxylalkyl,
(5) heterocyclyl, and
(6) unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl.

2. A compound of formula I according to claim 1, wherein $R^1$ is unsubstituted phenyl or phenyl substituted with 1 to 3 substituents independently selected from the group consisting of lower alkyl, halogen, lower halogenalkyl, hydroxy, lower alkoxy, lower halogenalkoxy and cyano.

3. A compound of formula I according to claim 1, wherein $R^1$ is unsubstituted phenyl or phenyl substituted with halogen.

4. A compound of formula I according to claim 1, wherein $R^2$, $R^3$, $R^4$ and $R^5$ independently from each other are hydrogen or halogen.

5. A compound of formula I according to claim 1, wherein $R^{2'}$ and $R^{3'}$ together as well as $R^{4'}$ and $R^{5'}$ together are replaced by a double bond.

6. A compound of formula I according to claim 1, wherein $R^6$ is selected from the group consisting of: (1) cycloalkyl, (2) lower alkoxyalkyl, (3) unsubstituted phenyl or phenyl substituted with 1 to 3 substituents independently selected from the group consisting of lower alkyl, halogen, lower halogenalkyl, lower alkoxy, lower halogenalkoxy and cyano, (4) lower phenylalkyl, (5) heterocyclyl selected from tetrahydrofuranyl and tetrahydropyranyl, and (6) pyridyl.

7. A compound of formula I according to claim 1, wherein $R^6$ is cycloalkyl.

8. A compound of formula I according to claim 1, wherein $R^6$ is unsubstituted phenyl or phenyl substituted with 1 to 3 substituents independently selected from the group consisting of lower alkyl, halogen, lower halogenalkyl, lower alkoxy, lower halogenalkoxy and cyano.

9. A compound of formula I according to claim 1, wherein $R^7$ is —C(O)—NH—$R^8$ and $R^8$ is selected from the group consisting of: (1) lower alkyl, (2) cycloalkyl, (3) lower cycloalkylalkyl, (4) cycloalkyl substituted by hydroxy, carboxyl, tetrazolyl or lower carboxylalkyl, (5) heterocyclyl, (6) unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl.

10. A compound of formula I according to claim 1, wherein $R^8$ is selected from the group consisting of: (1) unsubstituted cycloalkyl, (2) cycloalkyl substituted by hydroxy, (3) unsubstituted phenyl and (4) phenyl substituted with 1 to 3 substituents independently selected from the group consisting of lower alkyl, halogen, lower halogenalkyl, hydroxy, lower alkoxy, lower halogenalkoxy, carboxyl, lower alkoxycarbonyl, lower alkoxycarbonylalkyl, lower carboxylalkyl, lower carboxylalkoxy and lower alkoxycarbonylalkoxy.

11. A compound of formula I according to claim 1, wherein $R^7$ is —C(O)—$R^9$ and $R^9$ is selected from the group consisting of: (1) lower alkyl, (2) cycloalkyl, (3) lower cycloalkylalkyl, and (4) lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl.

12. A compound of formula I according to claim 1, wherein $R^9$ is lower cycloalkylalkyl.

13. A compound of formula I according to claim 1, wherein $R^7$ is —S(O)$_2$—$R^{10}$ and $R^{10}$ is selected from the group consisting of: (1) lower alkyl, (2) cycloalkyl, (3) lower cycloalkylalkyl, and (4) lower phenylalkyl, wherein the phenyl group of said phenylalkyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl.

14. A compound of formula I according to claim 13, wherein $R^{10}$ is lower cycloalkylalkyl.

15. A compound of formula I according to claim 1, wherein $R^7$ is —C(O)—O$R^{11}$ and $R^{11}$ is selected from the group consisting of: (1) lower alkyl, (2) cycloalkyl, (3) lower cycloalkylalkyl, (4) cycloalkyl substituted by hydroxy, carboxyl, tetrazolyl or lower carboxylalkyl, (5) heterocyclyl, (6) unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl.

16. A compound of claim 1, selected from the group consisting of:
1,3-dicyclohexyl-1-(2-phenyl-2H-indazol-3-yl)-urea,
4-[3-cyclohexyl-3-(2-phenyl-2H-indazol-3-yl)-ureido]-benzoic acid,
1-cyclohexyl-3-(2-fluoro-phenyl)-1-(2-phenyl-2H-indazol-3-yl)-urea,
1-cyclohexyl-3-(2,6-dimethyl-phenyl)-1-(2-phenyl-2H-indazol-3-yl)-urea,
1-benzyl-1-[2-(4-chloro-phenyl)-2H-indazol-3-yl]-3-cyclohexyl-urea,
3-[3-cyclohexyl-3-(2-phenyl-2H-indazol-3-yl)-ureido]-benzoic acid,
1-[2-(4-chloro-phenyl)-2H-indazol-3-yl]-3-cyclohexyl-1-(tetrahydro-pyran-4-yl)-urea,
1-[2-(4-chloro-phenyl)-2H-indazol-3-yl]-1,3-dicyclohexyl-urea,
4-{3-butyl-3-[2-(4-chloro-phenyl)-2H-indazol-3-yl]-ureido}-3-chloro-benzoic acid,
4-[3-cyclohexyl-3-(2-phenyl-2H-indazol-3-yl)-ureido]-3-methyl-benzoic acid,
3-chloro-4-[3-cyclohexyl-3-(2-phenyl-2H-indazol-3-yl)-ureido]-benzoic acid,
1-[2-(4-chloro-phenyl)-2H-indazol-3-yl]-3-cyclohexyl-1-phenyl-urea,
3-chloro-4-{3-[2-(4-chloro-phenyl)-5,6-difluoro-2H-indazol-3-yl]-3-cyclohexyl-ureido}-benzoic acid,
1-[2-(4-chloro-phenyl)-2H-indazol-3-yl]-3-cyclohexyl-1-(2-methoxy-ethyl)-urea,
3-chloro-4-{3-[2-(4-chloro-phenyl)-2H-indazol-3-yl]-3-phenyl-ureido}-benzoic acid methyl ester,
1-(3-chloro-phenyl)-1-[2-(4-chloro-phenyl)-2H-indazol-3-yl]-3-cyclohexyl-urea,
3-chloro-4-[3-[2-(4-chloro-phenyl)-2H-indazol-3-yl]-3-(2-methoxy-ethyl)-ureido]-benzoic acid,
(3-chloro-4-{3-[2-(4-chloro-phenyl)-2H-indazol-3-yl]-3-cyclohexyl-ureido}-phenyl)-acetic acid,
4-{3-[2-(4-chloro-phenyl)-2H-indazol-3-yl]-3-cyclohexyl-ureido}-3-methyl-benzoic acid,
3-chloro-4-{3-[2-(4-chloro-phenyl)-2H-indazol-3-yl]-3-cyclohexyl-ureido}-benzoic acid,
{4-[3-cyclohexyl-3-(2-phenyl-2H-indazol-3-yl)-ureido]-3-fluoro-phenoxy}-acetic acid,
1-[2-(4-chloro-phenyl)-2H-indazol-3-yl]-3-cyclohexyl-1-(3-ethoxy-phenyl)-urea,
3-(4-{3-[2-(4-chloro-phenyl)-2H-indazol-3-yl]-3-cyclohexyl-ureido}-3-fluoro-phenyl)-propionic acid,
3-{3-[2-(4-chloro-phenyl)-2H-indazol-3-yl]-3-cyclohexyl-ureido}-2-methyl-benzoic acid,
1-(3-chloro-4-fluoro-phenyl)-1-[2-(4-chloro-phenyl)-2H-indazol-3-yl]-3-cyclohexyl-urea,
1-[5-chloro-2-(4-chloro-phenyl)-2H-indazol-3-yl]-3-cyclohexyl-1-(3-ethoxy-phenyl)-urea,
(4-{3-[2-(4-chloro-phenyl)-2H-indazol-3-yl]-3-cyclohexyl-ureido}-3-fluoro-phenoxy)-acetic acid methyl ester,
3-chloro-4-{3-[2-(4-chloro-phenyl)-2H-indazol-3-yl]-3-cyclobutyl-ureido}-benzoic acid,
2-(4-{3-[2-(4-chloro-phenyl)-2H-indazol-3-yl]-3-cyclohexyl-ureido}-3-fluoro-phenyl)-2-methyl-propionic acid,
3-{3-[2-(4-chloro-phenyl)-2H-indazol-3-yl]-3-cyclohexyl-ureido}-4-methyl-benzoic acid,
N-[2-(4-chloro-phenyl)-2H-indazol-3-yl]-C-dicyclohexyl-methanesulfonamide,
1-(3-chloro-phenyl)-1-[2-(3-chloro-phenyl)-6-fluoro-2H-indazol-3-yl]-3-cyclohexyl-urea,
N-[2-(4-chloro-phenyl)-2H-indazol-3-yl]-2,N-dicyclohexyl-acetamide,
[2-(4-chloro-phenyl)-2H-indazol-3-yl]-cyclohexyl-carbamic acid cyclohexyl ester,
1-[2-(4-chloro-phenyl)-2H-indazol-3-yl]-1,3-dicyclopentyl-urea,
N-[2-(4-chloro-phenyl)-2H-indazol-3-yl]-N-cyclohexyl-2-phenyl-acetamide,
1-[2-(4-chloro-phenyl)-6-fluoro-2H-indazol-3-yl]-1,3-dicyclohexyl-urea,
trans-1-(3-chloro-phenyl)-1-[2-(4-chloro-phenyl)-2H-indazol-3-yl]-3-(4-hydroxy-cyclohexyl)-urea,
1-[2-(4-chloro-phenyl)-2H-indazol-3-yl]-3-cyclohexyl-1-pyridin-3-yl-urea,
1-(3-chloro-phenyl)-1-[2-(3-chloro-phenyl)-5,6-difluoro-2H-indazol-3-yl]-3-cyclohexyl-urea,
1-(3-chloro-phenyl)-1-[2-(4-chloro-phenyl)-6-fluoro-2H-indazol-3-yl]-3-cyclohexyl-urea,
1,3-dicyclohexyl-1-(2-phenyl-4,5,6,7-tetrahydro-2H-indazol-3-yl)-urea, and
3-chloro-4-[3-cyclohexyl-3-(2-phenyl-4,5,6,7-tetrahydro-2H-indazol-3-yl)-ureido]-benzoic acid, or
a pharmaceutically acceptable salt thereof.

17. A process for the preparation of a compound of formula I:

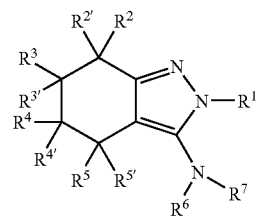

or a pharmaceutically acceptable salt thereof, wherein:
$R^1$ is a ring selected from the group consisting of phenyl, naphthyl and heteroaryl, said ring being unsubstituted or substituted with 1 to 3 substituents independently selected from the group consisting of: (1) lower alkyl, (2) halogen, (3) lower halogenalkyl, (4) hydroxy, (5) lower alkoxy, (6) lower halogenoalkoxy and (7) cyano;
$R^2$, $R^3$, $R^4$ and $R^5$ independently from each other are selected from the group consisting of hydrogen, halogen and lower alkyl;
$R^{2'}$ and $R^{3'}$ together as well as $R^{4'}$ and $R^{5'}$ together are replaced by a double bond, or $R^{2'}$, $R^{3'}$, $R^{4'}$ $R^{5'}$ are hydrogen;
$R^6$ is selected from the group consisting of:
(1) lower alkyl,
(2) cycloalkyl,
(3) lower alkoxyalkyl,
(4) unsubstituted phenyl or phenyl substituted with 1 to 3 substituents independently selected from the group consisting of lower alkyl, halogen, lower halogenalkyl, hydroxy, lower alkoxy, lower halogenoalkoxy, carboxyl, lower alkoxycarbonyl, lower alkoxycarbonylalkyl, lower carboxylalkoxy, lower alkoxycarbonlalkoxy and cyano,
(5) lower phenylalkyl, wherein the phenyl group is unsubstituted or substituted with 1 to 3 substitutents independently selected from the group consisting of lower alkyl, halogen, lower halogenalkyl, hydroxy, lower alkoxy, lower halogenalkoxy and cyano,
(6) heterocyclyl, and
(7) unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano;

$R^7$ is selected from the group consisting of:
(1) hydrogen, (2) —C(O)—NH—$R^8$, (3) —C(O)—$R^9$, (4) —S(O)$_2$—$R^{10}$, and (5) —C(O)—O$R^{11}$;

$R^8$ is selected from the group consisting of:
(1) lower alkyl,
(2) cycloalkyl,
(3) lower cycloalkylalkyl,
(4) cycloalkyl substituted by hydroxy, carboxyl, tetrazolyl or lower carboxylalkyl,
(5) heterocyclyl, and
(6) unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;

$R^9$ is selected from the group consisting of:
(1) lower alkyl,
(2) cycloalkyl,
(3) lower cycloalkylalkyl, and
(4) lower phenylalkyl, wherein the phenyl group of said lower phenylalkyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;

$R^{10}$ is selected from the group consisting of:
(1) lower alkyl,
(2) cycloalkyl,
(3) lower cycloalkylalkyl, and
(4) lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, caboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl; and $R^{11}$ is selected from the group consisting of:
(1) lower alkyl,
(2) cycloalkyl,
(3) lower cycloalkylalkyl,
(4) cycloalkyl substituted by hydroxy, carboxyl, tetrazolyl or lower carboxylalkyl,
(5) heterocyclyl, and
(6) unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl, which process comprises a) reductive amination of compound of formula II:

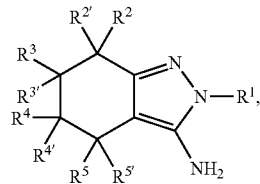

II $R^1$ to $R^{5'}$ are as defined above, with a ketone or aldehyde of formula III:

O=CR$^x$R$^y$    III, wherein CR$^x$R$^y$ corresponds to $R^6$ selected from the group consisting of (1) lower alkyl, (2) cycloalkyl, (3) lower alkoxyalkyl, (4) heterocyclyl, and (4) lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy and cyano, in the presence of a reducing agent and an acid to obtain a compound of formula Ic:

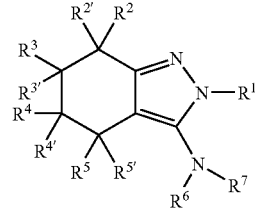

Ic wherein $R^1$ to $R^6$ are as defined above and $R^7$ is hydrogen, b) optionally transferring the compound of formula Ic into a compound of formula I, wherein $R^7$ is selected from a group consisting of —C(O)—NH—$R^8$, —C(O)—$R^9$, —S(O)$_2$—$R^{10}$ and —C(O)—O$R^{11}$ as defined in claim 1, and c) optionally converting the compound obtained into a pharmaceutically acceptable salt.

18. A process for the preparation of a compound of formula I:

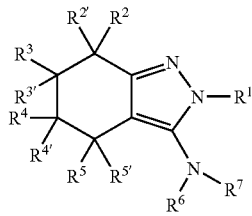

or a pharmaceutically acceptable salt thereof, wherein:
$R^1$ is a ring selected from the group consisting of phenyl, naphthyl and heteroaryl, said ring being unsubstituted or substituted with 1 to 3 substituents independently selected from the group consisting of: (1) lower alkyl, (2) halogen, (3) lower halogenalkyl, (4) hydroxy, (5) lower alkoxy, (6) lower halogenalkoxy and (7) cyano;
$R^2$, $R^3$, $R^4$ and $R^5$ independently from each other are selected from the group consisting of hydrogen, halogen and lower alkyl;
$R^{2'}$ and $R^{3'}$ together as well as $R^{4'}$ and $R^{5'}$ together are replaced by a double bond, or $R^{2'}$, $R^{3'}$, $R^{4'}$ and $R^{5'}$ are hydrogen;
$R^6$ is selected from the group consisting of:
  (1) lower alkyl,
  (2) cycloalkyl,
  (3) lower alkoxyalkyl,
  (4) unsubstituted phenyl or phen substituted with 1 to 3 substituents independently selected from the group consisting of lower alkyl, halogen, lower halogenalkyl, hydroxy, lower alkoxy, lower halogenalkoxy, carboxyl, lower alkoxycarbonyl, lower alkoxycarbonylalkyl, lower carboxylalkoxy, lower alkoxycarbonylalkoxy and cyano,
  (5) lower phenylalkyl, wherein the phenyl group is unsubstituted or substituted with 1 to 3 substituents independently selected from the group consisting of lower alkyl, halogen, lower halogenalkyl, hydroxy, lower alkoxy, lower halogenalkoxy and cyano,
  (6) heterocyclyl, and
  (7) unsubstituted heteroaryl or heteroaryl substituted with 1 to 3 substituents independently selected from the group consisting of lower alkyl, halogen, lower halogenalkyl, hydroxy, lower alkoxy, lower halogenalkoxy and cyano;
$R^7$ is selected from the group consisting of:
(1) hydrogen, (2) —C(O)—NH—$R^8$, (3) —C(O)—$R^9$, (4) —S(O)$_2$—$R^{10}$, and (5) —C(O)—$OR^{11}$;
$R^8$ is selected from the group consisting of:
  (1) lower alkyl,
  (2) cycloalkyl,
  (3) lower cycloalkylalkyl,
  (4) cycloalkyl substituted by hydroxy, carboxyl, tetrazolyl or lower carboxylalkyl,
  (5) heterocyclyl, an
  (6) unsubstituted phenyl or phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;
$R^9$ is selected from the group consisting of:
  (1) lower alkyl,
  (2) cycloalkyl,
  (3) lower cycloalkylalkyl, and
  (4) lower phenylalkyl, wherein the phenyl group of said lower phenylalkyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by carboxyl;
$R^{10}$ is selected from the group consisting of:
  (1) lower alkyl,
  (2) cycloalkyl,
  (3) lower cycloalkylalkyl, and
  (4) lower phenylalkyl, wherein the phenyl is unsubstituted or substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by caboxy; and
$R^{11}$ is selected from the group consisting of:
  (1) lower alkyl,
  (2) cycloalkyl,
  (3) lower cycloalkylalkyl,
  (4) cycloalkyl substituted by hydroxy, carboxyl, tetrazolyl or lower carboxylalkyl,
  (5) heterocyclyl, and
  (6) unsubstituted phenyl and phenyl substituted with 1 to 3 substituents independently selected from the group consisting of lower alkyl, halogen, lower halogenalkyl, hydroxy, lower alkoxy, lower halogenalkoxy, carboxyl, tetrazolyl, lower alkoxycarbonyl, lower alkoxycarbonylalkyl, lower carboxylalkyl, lower carboxylalkoxy, lower alkoxycarbonylalkoxy, cyano and cycloalkyloxy wherein the cycloalkyl group of said cycloalkyloxy is substituted by caboxyl,
which process comprises:
a) nucleophilic aromatic substitution of a compound of formula IV:

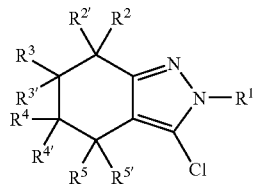

wherein $R^1$ to $R^{5'}$ is defined as above, with an amine of the formula V:

$R^6$—NH$_2$  V, wherein $R^6$ is defined as above, to obtain a compound of formula Ic:

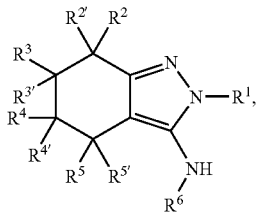

wherein $R^1$ to $R^6$ are as defined in claim 1, b) optionally transferring the compound of formula Ic into a compound of formula I, wherein $R^7$ is selected from a group consisting of —C(O)—NH—$R^8$, —C(O)—$R^9$, —S(O)$_2$—$R^{10}$ and —C(O)—O$R^{11}$ as defined in claim 1, and c) optionally converting the compound obtained into a pharmaceutically acceptable salt.

19. A pharmaceutical composition comprising a compound of claim 1 and a pharmaceutically acceptable excipient.

20. A compound selected from the group consisting of:
1-butyl-1-[2-(4-chloro-phenyl)-2H-indazol-3-yl]-3-cyclohexyl-urea,
benzyl-(2-phenyl-2-indazol-3-yl)-amine,
4-{3-butyl-3-[2-(4-chloro-phenyl)-2H-indazol-3-yl]-ureido}-3-chloro-benzoic acid, and
cyclohexyl-2-phenyl-4,5,6,7-tetrahydro-2H-indazol-3-yl)-amine.

* * * * *